(12) United States Patent
Anderson et al.

(10) Patent No.: US 10,342,783 B2
(45) Date of Patent: *Jul. 9, 2019

(54) COMPOUNDS $\alpha_v\beta_6$ INTEGRIN ANTAGONISTS

(71) Applicant: GlaxoSmithKline Intellectual Property Development Limited, Brentford, Middlesex (GB)

(72) Inventors: Niall Andrew Anderson, Stevenage (GB); Matthew Howard James Campbell-Crawford, Stevenage (GB); Ashley Paul Hancock, Stevenage (GB); John Martin Pritchard, Stevenage (GB); Joanna Mary Redmond, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,674

(22) Filed: Mar. 15, 2018

(65) Prior Publication Data
US 2018/0271845 A1    Sep. 27, 2018

Related U.S. Application Data

(63) Continuation of application No. 15/514,399, filed as application No. PCT/EP2015/071776 on Sep. 22, 2015, now Pat. No. 9,956,209.

(30) Foreign Application Priority Data

Sep. 26, 2014 (GB) .................. 1417002.1

(51) Int. Cl.
*A61K 31/4375* (2006.01)
*C07D 471/04* (2006.01)
*A61K 31/19* (2006.01)

(52) U.S. Cl.
CPC ........ *A61K 31/4375* (2013.01); *C07D 471/04* (2013.01); *A61K 31/19* (2013.01)

(58) Field of Classification Search
CPC .......................... C07D 471/04; A61K 31/4375
USPC ........................................................ 546/122
See application file for complete search history.

(56) References Cited

U.S. PATENT DOCUMENTS 9,956,209 B2 * 5/2018 Anderson ............ C07D 471/04
2004/0092454 A1   5/2004 Schadt et al.

FOREIGN PATENT DOCUMENTS

| WO | WO 99/30709 A1 | 6/1999 |
|---|---|---|
| WO | WO 99/31061 A1 | 6/1999 |
| WO | WO 00/72801 A2 | 12/2000 |
| WO | WO 00/78317 A1 | 12/2000 |
| WO | WO 01/24797 A1 | 4/2001 |
| WO | WO 01/34602 A2 | 5/2001 |
| WO | WO 03/039544 A1 | 5/2001 |
| WO | WO 01/096334 A2 | 12/2001 |
| WO | WO 02/07730 A1 | 1/2002 |
| WO | WO 02/22616 A2 | 3/2002 |
| WO | WO 02/053099 A2 | 7/2002 |
| WO | WO2004/058254 A1 | 7/2004 |
| WO | WO 2004/092454 A2 | 10/2004 |
| WO | WO 2005/082889 A1 | 9/2005 |
| WO | WO 2008/118455 A1 | 10/2008 |
| WO | WO 2009/018466 A1 | 2/2009 |
| WO | WO 2009/055418 A1 | 4/2009 |
| WO | WO 2011/111880 A1 | 9/2011 |
| WO | WO 2014/154725 A1 | 10/2014 |
| WO | WO 2015/048819 A1 | 4/2015 |
| WO | WO 2016/046225 A1 | 3/2016 |
| WO | WO 2016/046226 A1 | 3/2016 |
| WO | WO 2016/046230 A1 | 3/2016 |
| WO | WO 2016/046241 A1 | 3/2016 |
| WO | WO 2016/134223 A2 | 8/2016 |
| WO | WO 2016/145258 A1 | 9/2016 |
| WO | WO 2017/158072 A1 | 9/2017 |
| WO | WO 2017/162570 A1 | 9/2017 |

OTHER PUBLICATIONS

Cho et al., "Pirfenidone: an anti-fibrotic and cytoprotective agent as therapy for progressive kidney disease", *Expert Opin. Investig. Drugs*, vol. 19, No. 2, pp. 275-283 (2010).

Goodman et al., "Integrins as therapeutic targets", *Trends in Pharmacological Sciences*, vol. 33, No. 7, pp. 405-412 (2012).

Hahm et al., "avB6 integrin Regulates Renal Fibrosis and Inflammation in Alport Mouse", *The American Journal of Pathology*, vol. 170, No. 1, pp. 110-125 (2007).

Horan et al., "Partial Inhibition of Integrin avB6 Prevents Pulmonary Fibrosis without Exacerbating Inflammation", *Am. J. Respir. Crit. Care Med.*, vol. 177, pp. 56-65 (2008).

Margadant, C. et al., "Integrin-TGF-β crosstalk in fibrosis, cancer, and wound healing", *EMBO Reports*, vol. 11, No. 2, pp. 97-105 (2010).

(Continued)

*Primary Examiner* — Niloofar Rahmani
(74) *Attorney, Agent, or Firm* — Jane F. Djung; Duke M. Fitch; Edward R. Gimmi

(57) ABSTRACT

A compound of formula (I):

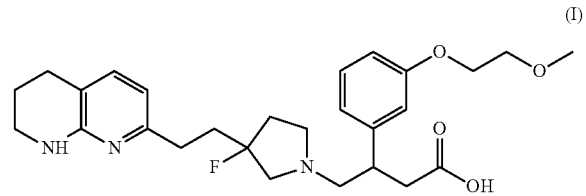

being 4-(3-Fluoro-3-(2-(5,6,7,8-tetrahydro-1,8-naphthyridin-2-yl) ethyl) pyrrolidin-1-yl)-3-(3-(2-methoxyethoxy) phenyl) butanoic acid, or a salt thereof.

38 Claims, 1 Drawing Sheet

(56) References Cited

OTHER PUBLICATIONS

Popov et al, "Integrin avB6 is a marker of the progression of biliary and portal liver fibrosis and a novel target for antifibrotic therapies", *Journal of Hepatology*, vol. 48 pp. 453-464 (2008).
Trevillian et al., "$\alpha_v\beta_6$ integrin expression in diseased and transplanted kidneys", *Kidney International*, vol. 66, pp. 1423-1433 (2004).
Whitman et al., "Nonpeptide $\alpha v$ $\beta 3$ antagonists. Part 9: Improved pharmacokinetic profile through the use of an aliphatic, des-amide backbone", *Bioorganic & Medicinal Chemistry Letters*, vol. 14, No. 17, pp. 4411-4415 (2004).
Woodcock, et al. The treatment of idiopathic pulmonary fibrosis, *F1000Prime Reports*, vol. 6, No. 16, pp. 1-9 (2014).
International Search Report for International Application No. PCT/EP2014/056013, dated May 9, 2014, 4 pages.
International Search Report for International Application No. PCT/EP2015/071776, Nov. 5, 2015 (date of completion of the international search).
International Search Report for International Application No. PCT/EP2015/071777, dated Nov. 26, 2015, 3 pages.
International Search Report for International Application No. PCT/EP2015/071782, dated Nov. 2, 2015, 4 pages
International Search Report for International application No. PCT/EP2015/071798, dated Nov. 10, 2015, 4 pages.
International Search Report for International application No. PCT/EP2017/056525, dated May 2, 2017, 4 pages.
International Search Report for International application No. PCT/EP2017/056527, dated May 2, 2017, 5 pages.
International Search Report for International application No. PCT/EP2017/056204, dated May 15, 2017, 5 pages.
Restriction Requirement for U.S. Appl. No. 14/778,095, USPTO, dated Sep. 21, 2016, 9 pages.
Non-Final Office Action for U.S. Appl. No. 14/778,095, USPTO, dated Mar. 29, 2017, 14 pages.
Notice of Allowance for U.S. Appl. No. 14/778,095, USPTO, dated Nov. 3, 2017, 11 pages.
Notice of Allowance for U.S. Appl. No. 15/514,407, USPTO, dated Nov. 6, 2017, 16 pages.
Restriction Requirement for U.S. Appl. No. 15/514,416, USPTO, dated Aug. 14, 2017, 12 pages.
Non-Final Office Action for U.S. Appl. No. 15/514,416, USPTO, dated Nov. 2, 2017, 18 pages.
Notice of Allowance for U.S. Appl. No. 15/514,414, USPTO, dated Nov. 9, 2017, 19 pages.

* cited by examiner

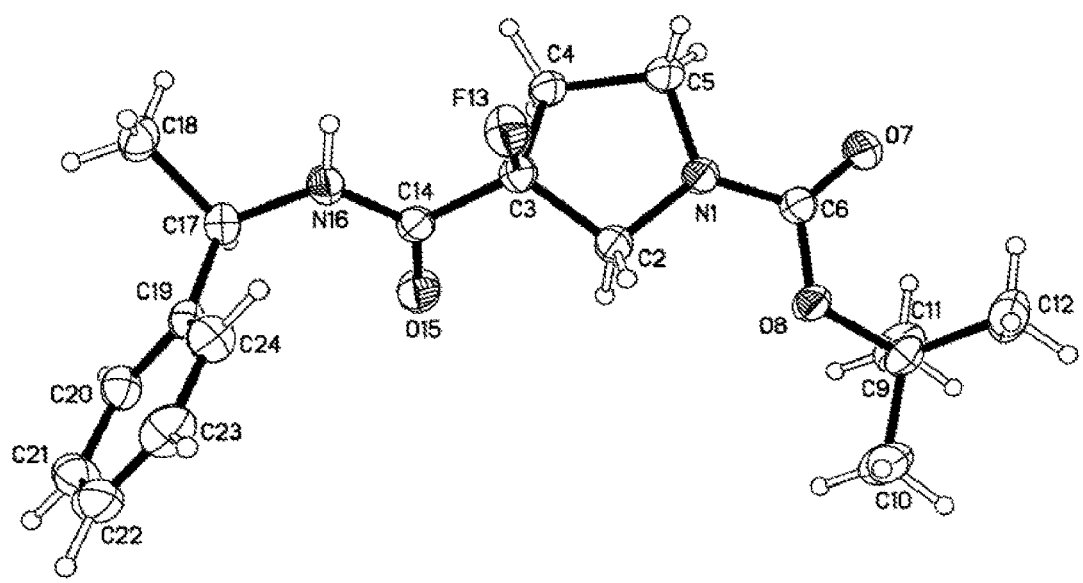

COMPOUNDS $\alpha_v\beta_6$ INTEGRIN ANTAGONISTS

FIELD OF THE INVENTION

The present invention relates to pyrrolidine compounds being $\alpha_v\beta_6$ integrin antagonists, pharmaceutical compositions comprising such compounds and to their use in therapy, especially in the treatment of conditions for which an $\alpha_v\beta_6$ integrin antagonist is indicated, for the use of a compound in the manufacture of a medicament for the treatment of conditions in which an antagonist of $\alpha_v\beta_6$ integrin is indicated and a method for the treatment or prophylaxis of disorders in which antagonism of $\alpha_v\beta_6$ integrin is indicated in a human.

BACKGROUND OF THE INVENTION

Integrin superfamily proteins are heterodimeric cell surface receptors, composed of an alpha and beta subunit. At least 18 alpha and 8 beta subunits have been reported, which have been demonstrated to form 24 distinct alpha/beta heterodimers. Each chain comprises a large extracellular domain (>640 amino acids for the beta subunit, >940 amino acids for the alpha subunit), with a transmembrane spanning region of around 20 amino acids per chain, and generally a short cytoplasmic tail of 30-50 amino acids per chain. Different integrins have been shown to participate in a plethora of cellular biologies, including cell adhesion to the extracellular matrix, cell-cell interactions, and effects on cell migration, proliferation, differentiation and survival (Barczyk et al, *Cell and Tissue Research*, 2010, 339, 269).

Integrin receptors interact with binding proteins via short protein-protein binding interfaces. The integrin family can be grouped into sub-families that share similar binding recognition motifs in such ligands. A major subfamily is the RGD-integrins, which recognise ligands that contain an RGD (arginine-glycine-aspartic acid) motif within their protein sequence. There are 8 integrins in this subfamily, namely $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_5\beta_1$, $\alpha_8\beta_1$, where nomenclature demonstrates that $\alpha_v\beta_1$, $\alpha_v\beta_3$, $\alpha_v\beta_5$, $\alpha_v\beta_6$, & $\alpha_v\beta_8$ share a common av subunit with a divergent β subunit, and $\alpha_v\beta_1$, $\alpha_5\beta_1$ & $\alpha_8\beta_1$ share a common $\beta_1$ subunit with a divergent a subunit. The $\beta_1$ subunit has been shown to pair with 11 different α subunits, of which only the 3 listed above commonly recognise the RGD peptide motif (Humphries et al, *Journal of Cell Science*, 2006, 119, 3901).

The 8 RGD-binding integrins have different binding affinities and specificities for different RGD-containing ligands. Ligands include proteins such as fibronectin, vitronectin, osteopontin, and the latency associated peptides (LAPs) of Transforming Growth Factor $\beta_1$ and $\beta_3$ (TGF$\beta_1$ and TGF$\beta_3$). Integrin binding to the LAPs of TGF$\beta_1$ and TGF$\beta_3$ has been shown in several systems to enable activation of the TGF$\beta_1$ and TGF$\beta_3$ biological activities, and subsequent TGFβ-driven biologies (Worthington et al, *Trends in Biochemical Sciences*, 2011, 36, 47). The diversity of such ligands, coupled with expression patterns of RGD-binding integrins, generates multiple opportunities for disease intervention. Such diseases include fibrotic diseases (Margadant et al, *EMBO reports*, 2010, 11, 97), inflammatory disorders, cancer (Desgrosellier et al, *Nature Reviews Cancer*, 2010, 10, 9), restenosis, and other diseases with an angiogenic component (Weis et al, *Cold Spring. Harb. Perspect. Med.* 2011, 1, a 006478).

A significant number of $\alpha_v$ integrin antagonists (Goodman et al, *Trends in Pharmacological Sciences*, 2012, 33, 405) have been disclosed in the literature including inhibitory antibodies, peptides and small molecules. For antibodies these include the pan-$\alpha_v$ antagonists Intetumumab and Abituzumab (Gras, *Drugs of the Future*, 2015, 40, 97), the selective $\alpha_v\beta_3$ antagonist Etaracizumab, and the selective $\alpha_v\beta_6$ antagonist STX-100. Cilengitide is a cyclic peptide antagonist that inhibits both $\alpha_v\beta_3$ and $\alpha_v\beta_5$ and SB-267268 is an example of a compound (Wilkinson-Berka et al, *Invest. Ophthalmol. Vis. Sci.*, 2006, 47, 1600), that inhibits both $\alpha_v\beta_3$ and $\alpha_v\beta_5$. Invention of compounds to act as antagonists of differing combinations of $\alpha_v$ integrins enables novel agents to be generated tailored for specific disease indications.

Pulmonary fibrosis represents the end stage of several interstitial lung diseases, including the idiopathic interstitial pneumonias, and is characterised by the excessive deposition of extracellular matrix within the pulmonary interstitium. Among the idiopathic interstitial pneumonias, idiopathic pulmonary fibrosis (IPF) represents the commonest and most fatal condition with a typical survival of 3 to 5 years following diagnosis. Fibrosis in IPF is generally progressive, refractory to current pharmacological intervention and inexorably leads to respiratory failure due to obliteration of functional alveolar units. IPF affects approximately 500,000 people in the USA and Europe.

There are in vitro experimental, animal and IPF patient immunohistochemistry data to support a key role for the epithelially restricted integrin, $\alpha_v\beta_6$, in the activation of TGFβ1. Expression of this integrin is low in normal epithelial tissues and is significantly up-regulated in injured and inflamed epithelia including the activated epithelium in IPF. Targeting this integrin, therefore, reduces the theoretical possibility of interfering with wider TGFβ homeostatic roles. Partial inhibition of the $\alpha_v\beta_6$ integrin by antibody blockade has been shown to prevent pulmonary fibrosis without exacerbating inflammation (Horan G S et al Partial inhibition of integrin $\alpha_v\beta_6$ prevents pulmonary fibrosis without exacerbating inflammation. *Am J Respir Crit Care Med* 2008 177: 56-65). Outside of pulmonary fibrosis, $\alpha_v\beta_6$ is also considered an important promoter of fibrotic disease of other organs, including liver and kidney (Reviewed in Henderson N C et al Integrin-mediated regulation of TGFβ in Fibrosis, Biochimica et Biophysica Acta—Molecular Basis of Disease 2013 1832:891-896), suggesting that an $\alpha_v\beta_6$ antagonist could be effective in treating fibrotic diseases in multiple organs.

Consistent with the observation that several RGD-binding integrins can bind to, and activate, TGFβ, different $\alpha_v$ integrins have recently been implicated in fibrotic disease (Henderson N C et al Targeting of $\alpha_v$ integrin identifies a core molecular pathway that regulates fibrosis in several organs *Nature Medicine* 2013 Vol 19, Number 12: 1617-1627; Sarrazy V et al Integrins αvβ5 and αvβ3 promote latent TGF-β1 activation by human cardiac fibroblast contraction *Cardiovasc Res* 2014 102:407-417; Minagawa S et al Selective targeting of TGF-β activation to treat fibroinflammatory airway disease *Sci Transl Med* 2014 Vol 6, Issue 241: 1-14; Reed N I et al. The $\alpha_v\beta_1$ integrin plays a critical in vivo role in tissue fibrosis *Sci Transl Med* 2015 Vol 7, Issue 288: 1-8). Therefore inhibitors against specific members of the RGD binding integrin families, or with specific selectivity fingerprints within the RGD binding integrin family, may be effective in treating fibrotic diseases in multiple organs.

SAR relationships of a series of integrin antagonists against $\alpha_v\beta_3$ $\alpha_v\beta_5$, $\alpha_v\beta_6$ and $\alpha_v\beta_8$ have been described (Macdonald, S J F et al. Structure activity relationships of $\alpha_v$ integrin antagonists for pulmonary fibrosis by variation in aryl substituents. *ACS Med Chem Lett* 2014, 5, 1207-1212. 19 Sep. 2014).

It is an object of the invention to provide $\alpha_v\beta_6$ inhibitors, preferably with activities against other $\alpha_v$ integrins, such as $\alpha_v\beta_1$, $\alpha_v\beta_3$, $\alpha_v\beta_5$ or $\alpha_v\beta_8$.

BRIEF SUMMARY OF THE INVENTION

In a first aspect of the present invention, there is provided a compound of formula (I), 4-(3-fluoro-3-(2-(5,6,7,8-tetrahydro-1, 8-naphthyridin-2-yl) ethyl) pyrrolidin-1-yl)-3-(3-(2-methoxyethoxy) phenyl) butanoic acid or a salt thereof, more particularly a compound of formula (I) or a pharmaceutically acceptable salt thereof:

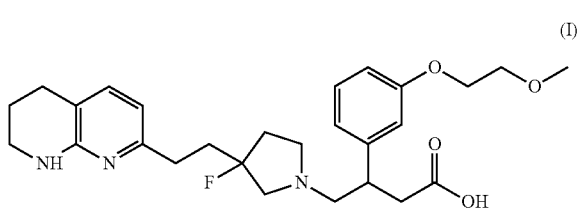 [SMILES: COCCOc1cccc(C(CC(=O)O)CN2CCC(F)(CCc3ccc4c(n3)NCCC4)C2)c1]

(I)

Compounds of formula (I) and their salts have $\alpha_v\beta_6$ antagonist activity and are believed to be of potential use for the treatment or prophylaxis of certain disorders.

The term $\alpha_v\beta_6$ antagonist activity includes $\alpha_v\beta_6$ inhibitor activity herein.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of a disease or condition for which an $\alpha_v\beta_6$ integrin receptor antagonist is indicated.

In a fourth aspect of the present invention, there is provided a method of treatment or prophylaxis of a disease or condition for which an $\alpha_v\beta_6$ integrin receptor antagonist is indicated in a human in need thereof which comprises administering to a human in need thereof a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of a disease or condition for which an $\alpha_v\beta_6$ integrin receptor antagonist is indicated.

BRIEF DESCRIPTION OF THE DRAWINGS

FIG. 1 shows the X-ray crystal structure of compound (XVIII).

DETAILED DESCRIPTION OF THE INVENTION

In a first aspect of the present invention, there is provided a compound of formula (I), 4-(3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid, or a salt thereof, more particularly a compound of formula (I) or a pharmaceutically acceptable salt thereof:

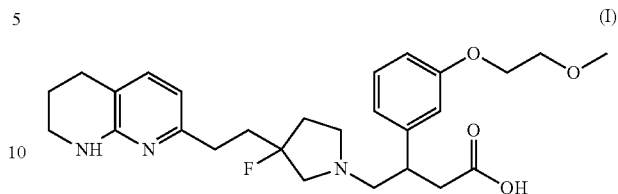

(I)

In another embodiment the compound of Formula (I) is a pharmaceutically acceptable salt of 4-(3-fluoro-3-(2-(5,6,7,8-tetra hydro-1,8-naphthyridin-2-yl)ethyl)pyrrolidin-1-yl)-3-(3-(2-methoxyethoxy)phenyl)butanoic acid.

In another embodiment the compound of Formula (I) is 4-(3-fluoro-3-(2-(5,6,7,8-tetrahydro-1,8-naphthyridin-2-yl) ethyl)pyrrolidin-1-yl)-3-(3-(2-methoxyethoxy)phenyl)butanoic acid.

In an embodiment the compound of formula (I) has the formula (IA1):

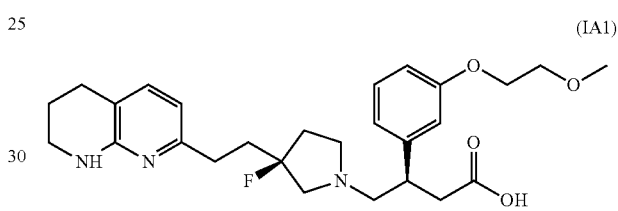

(IA1)

being (R)-4-((S)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid or a pharmaceutically acceptable salt thereof.

In an embodiment the compound of formula (I) has the formula (IA2):

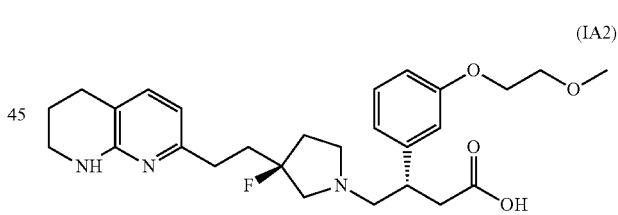

(IA2)

being (S)-4-((S)-3-Fluoro-3-(2-(5,6,7,8-tetrahydro-1,8-naphthyridin-2-yl) ethyl) pyrrolidin-1-yl)-3-(3-(2-methoxyethoxy) phenyl) butanoic acid or a pharmaceutically acceptable salt thereof In an embodiment the compound of formula (I) has the formula (IA3):

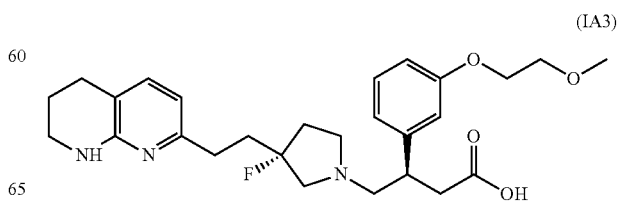

(IA3)

being (R)-4-((R)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid or a pharmaceutically acceptable salt thereof.

In an embodiment the compound of formula (I) has the formula (IA4):

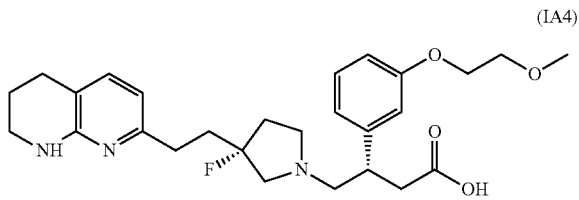 [SMILES: COCCOc1cccc([C@H](CC(=O)O)CN2CC[C@](F)(CCc3ccc4c(n3)NCCC4)C2)c1]

(IA4)

being (S)-4-((R)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid or a pharmaceutically acceptable salt thereof.

In another embodiment the compound of Formula (I) or any one of compounds IA1, IA2, IA3 or IA4 is a pharmaceutically acceptable salt of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid.

Compounds of formula (I) have both a basic amine group and a carboxylic acid group and can consequently form an internal salt i.e. a zwitterion or inner salt. Therefore in an embodiment the compound of formula (I) is 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid or any one of compounds IA1, IA2, IA3 or IA4 in a zwitterion salt form. In another embodiment, the compound of formula (I) is 4-(3-fluoro-3-(2-(5,6,7,8-tetrahydro-1,8-naphthyridin-2-yl)ethyl)pyrrolidin-1-yl)-3-(3-(2-methoxyethoxy)phenyl) butanoic acid or any one of compounds IA1, IA2, IA3 or IA4 in a non-zwitterionic form.

It will be appreciated that the present invention covers compounds of formula (I), IA1, IA2, IA3 or IA4 as the parent compound, as a zwitterion (the parent compound is protonated internally by its carboxylic acid group and normally exists as a zwitterion) and as salts thereof, for example as a pharmaceutically acceptable salt thereof.

For a review on suitable salts see Berge et al., *J. Pharm. Sci.*, 66:1-19, (1977). Suitable pharmaceutically acceptable salts are listed in P H Stahl and C G Wermuth, editors, *Handbook of Pharmaceutical Salts; Properties, Selection and Use*, Weinheim/Zurich: Wiley-VCH/VHCA, 2002. Suitable pharmaceutically acceptable salts can include acid addition salts with inorganic acids such, for example, as hydrochloric acid, hydrobromic acid, orthophosphoric acid, nitric acid, phosphoric acid, or sulphuric acid, or with organic acids such, for example as methanesulphonic acid, ethanesulphonic acid, p-toluenesulphonic acid, acetic acid, propionic acid, lactic acid, citric acid, fumaric acid, malic acid, succinic acid, salicylic acid, maleic acid, glycerophosphoric acid, tartaric, benzoic, glutamic, aspartic, benzenesulphonic, naphthalenesulphonic such as 2-naphthalenesulphonic, hexanoic acid or acetylsalicylic acid, in particular, maleic acid. Typically, a pharmaceutically acceptable salt may readily be prepared by using a desired acid or base as appropriate. The resultant salt may precipitate from solution and be collected by filtration or may be recovered by evaporation of the solvent.

Other non-pharmaceutically acceptable salts, e.g. formates, oxalates or trifluoroacetates, may be used, for example in the isolation of the compounds of formula (I), and are included within the scope of this invention.

A pharmaceutically acceptable base addition salt can be formed by reaction of a compound of formula (I) with a suitable organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable inorganic base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

In one embodiment the compound of formula (I) is in the form of the parent compound, for example 4-(3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid.

The invention includes within its scope all possible stoichiometric and non-stoichiometric forms of the salts of the compounds of formula (I).

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds of formula (I) may also be prepared as an amorphous molecular dispersion in a polymer matrix, such as hydroxypropylmethyl cellulose acetate succinate, using a spray-dried dispersion (SDD) process to improve the stability and solubility of the drug substance.

The compounds of formula (I) may also be delivered using a liquid encapsulation technology to improve properties such as bioavailability and stability, in either liquid or semi-solid filled hard capsule or soft gelatin capsule formats.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. It will be appreciated that crystalline forms optionally may be solvated to form, for example, pharmaceutically acceptable solvates, such as hydrates which may be stoichiometric hydrates as well as compounds containing variable amounts of water. Solvates include stoichiometric solvates and non-stoichiometric solvates. Compounds of formula (I) may exist in solvated or non-solvated form.

The compounds described herein contain two asymmetric centres so that optical isomers, e.g. diastereoisomers and enantiomers may be formed. Accordingly, the present invention encompasses isomers of the compounds of formula (I) whether as individual isomers isolated such as to be substantially free of the other isomer (i.e. pure) or as mixtures. An individual isomer isolated such as to be substantially free of the other isomer (i.e. pure) may be isolated such that less than 10%, particularly less than about 1%, for example less than about 0.1% of the other isomer is present.

It will be understood by those skilled in the art that certain diastereoisomers may be less active than others and that the activity of an individual diastereoisomer may fall below a selected limit.

Separation of isomers may be achieved by conventional techniques known to those skilled in the art, e.g. by fractional crystallisation, chromatography, HPLC or a combination of these techniques.

Compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

It will be appreciated by those skilled in the art that the (E) or (Z) description of some intermediate compounds which can exist in two geometrical isomers, may contain the other geometric isomer as a minor component.

Compounds of structural formula (I) may be prepared by a process involving first deprotection of a compound of structural formula (II), i.e. cleavage of the ester group, followed optionally by conversion to a salt:

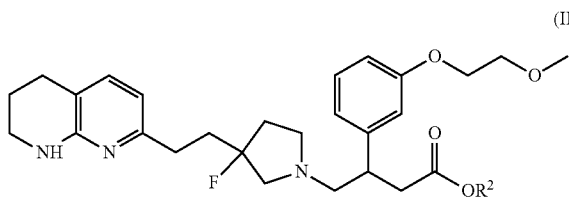

(II)

where $R^2$ is a $C_1$-$C_6$ alkyl group for example a tert-butyl, ethyl or methyl group. Alternatively $R^2$ is a chiral alkyl for example (−)-menthyl [(1R,2S,5R)-2-isopropyl-5-methylcyclohexanol].

A sixth aspect of the invention provides a compound of formula (II).

The deprotection of compound of structural formula (II) where $R^2$ is methyl, ethyl, a chiral alkyl such as menthyl or tert-Bu may be accomplished by acid hydrolysis using for example hydrochloric, hydrobromic, sulphuric, or trifluoroacetic acid, in an inert solvent, such as dichloromethane, 2-methyl-tetra hydrofuran, tetrahydrofuran, 1,4-dioxane or cyclopentyl methyl ether or water.

Alternatively the deprotection of compound of structural formula (II) where $R^2$ is methyl, ethyl or a chiral alkyl such as menthyl may be accomplished by base hydrolysis using for example lithium hydroxide, sodium hydroxide, potassium hydroxide in a suitable solvent, e.g. an aqueous solvent such as aqueous methanol.

After the cleavage of the ester group the resulting product may be converted to the required salt by methods well known to those skilled in the art.

In one embodiment the conversion of the zwitterion to the hydrochloride slat is achieved by treatment of a solution of the zwitterion in an inert organic solvent such as acetonitrile or acetone with an aqueous hydrochloric acid solution, concentration of the resulting salt solution and crystallisation from acetonitrile.

In one embodiment the conversion of the zwitterion to the maleate salt is achieved by treatment of an acetonitrile solution of the zwitterion with an aqueous solution of maleic acid, heating the resulting solution to 40° C. and allowing to cool to 5° C. for crystallisation to occur.

Compounds of structural formula (II) may be obtained from compounds of structural formula (III):

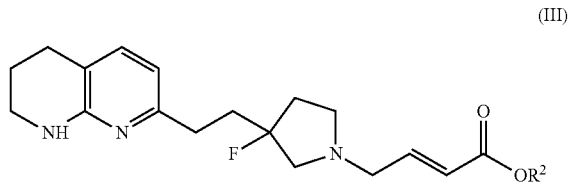

(III)

where $R^2$ is as defined above, by reaction with a boronic acid compound of structural formula (IV):

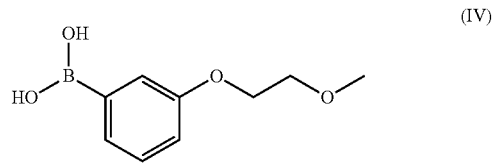

(IV)

Alternatively a boronate ester, such as pinacol ester may be used, which provides the parent boronic acid in situ. Compounds of structural formula (IV) are commercially available e.g. from Enamine LLC, Princeton Corporate Plaza, 7 Deer Park Drive Ste. 17-3, Monmouth Jct. NJ (USA) 08852, Manchester Organics or Fluorochem. The reaction between the compound of structural formulae (III) and (IV) may be performed in the presence of a suitable catalyst, such as a rhodium catalyst, for example the dimer of rhodium (1,5-cyclooctadiene) chloride, [Rh(COD)Cl]$_2$ and an additive such as a phosphine ligand, for example bis(diphenylphosphino)-1,1'-binaphthyl (BINAP), preferably in the presence of a base, such as aqueous potassium hydroxide, at elevated temperature, such as 50-90° C., and in a water-miscible solvent, such as 1,4-dioxane. The reaction is preferably carried out under strictly anaerobic conditions, where the reaction mixture is purged with an inert gas such as nitrogen, and evacuated under reduced pressure, repeating this process of evacuation and purging with nitrogen three times. This reaction produces a mixture of isomers, normally in the ratio of 1:1. The mixture of isomers produced can be separated by chromatography, HPLC or by crystallisation. An asymmetric synthesis can be achieved by inclusion of one enantiomer of the chiral ligand 2,2'-bis(diphenylphosphino)-1,1'-binaphthyl ("BINAP") in the presence of a catalyst based on a rhodium compound. The geometry of the double bond in the compound of structural formula (III) may be (E) or mixture of (E) and (Z) isomers, preferably pure (E) isomer.

The reaction between one enantiomer of a compound of formula (III) with a compound of formula (IV) produces two diastereoisomers in approximately 1:1 ratio, which can be separated by crystallisation, chromatography, or by HPLC. A preferred method of separation is chiral HPLC on a chiral support, such as Chiralpak or Chiralcel columns. The ratio of the diastereoisomers formed can be increased substantially to for example approximately 80:20 or higher, in the presence of about 10% of additives, such as (R)-(+)-2,2'-bis(diphenylphosphino)-1,1'-binaphthalene [(R)-BINAP], which provides as the major isomer the biologically more active diastereoisomer.

Alternatively, various combinations of compound (III) with different chiral R² groups, ligand, boronic acid (IV), catalyst and solvent selected by those skilled in the art or by screening large numbers of combinations may afford a higher ratio of diastereoisomers.

The diastereoisomeric ratio may be further increased to, for example, greater than 99:1, by chiral HPLC, or by crystallisation.

Compounds of structural formula (III) may be obtained from compounds of structural formula (V):

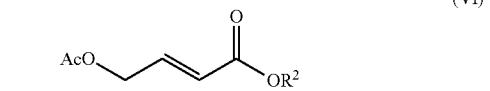

(V)

by reaction with a compound of structural formula (VI)

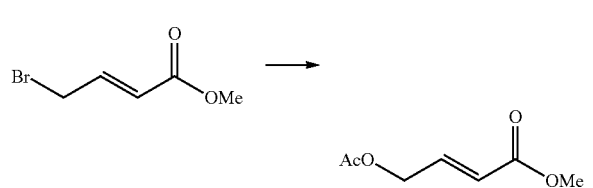

(VI)

where R² is as defined above, in the presence of an organic base such as N,N-diisopropylethylamine ("DIPEA") and a suitable palladium-based catalyst, for example PdCl₂(dppf)-CH₂Cl₂ [1,1'-bis(diphenylphosphino) ferrocene]dichloropalladium(II), complex with dichloromethane, in a solvent such as dichloromethane. The compound of formula (V) can be used as the parent compound, or be generated in situ from a salt, such as the dihydrochloride salt, in the presence of a tertiary amine base.

Compounds of structural formula (VI) may be prepared by methods described herein. By way of illustration compound of structural formula (VI), where R² is methyl, and the double bond having the (E) geometry, can be prepared by the method shown below, starting from the commercially available methyl 4-bromocrotonate and sodium or potassium acetate in acetonitrile at elevated temperature e.g. 50° C.:

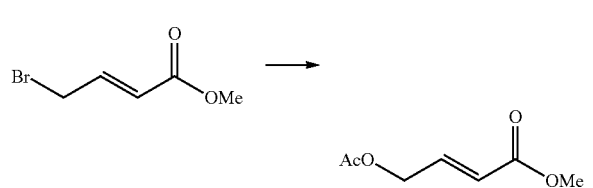

Compounds of structural formula (V) may be prepared from compounds of structural formula (VII):

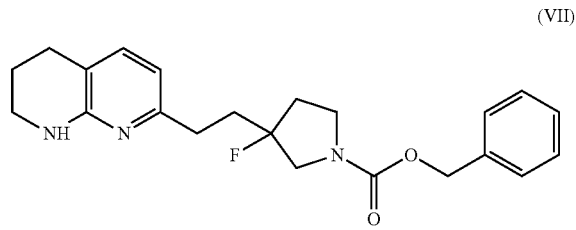 [SMILES: O=C(OCc1ccccc1)N1CCC(F)(CCc2ccc3c(n2)NCCC3)C1]

(VII)

by catalytic hydrogenolysis for example using a palladium catalyst deposited on carbon, in an inert solvent, such as ethanol or ethyl acetate.

Compounds of structural formula (VII) may be obtained from compounds of structural formula (VIII):

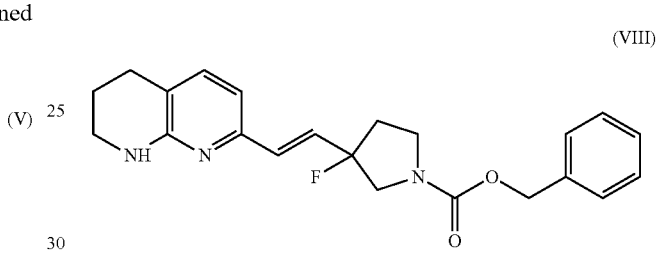

(VIII)

by diimide reduction, generated for example from benzenesulfonyl hydrazide in the presence of a base, such as potassium carbonate, in a suitable solvent, such as DMF, and at elevated temperature, such as 130° C.

Compounds of structural formula (VIII) exist as geometrical isomers e.g. (E) or (Z)-form and may be used either as pure isomers or as mixtures. Compounds of structural formula (VIII) may be obtained starting from known commercially available (e.g. from Wuxi App Tec, 288 Fute Zhong Road, Waigaoquiao Free Trade, Shanghai 200131, China) compounds of structural formula (IX):

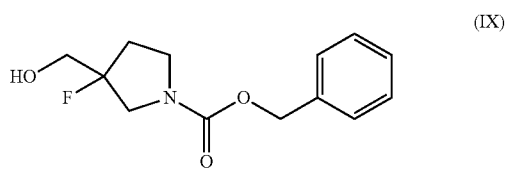 [SMILES: O=C(OCc1ccccc1)N1CCC(F)(CO)C1]

(IX)

which may be oxidised e.g. with sulphur trioxide in pyridine to the corresponding aldehyde of structural formula (X):

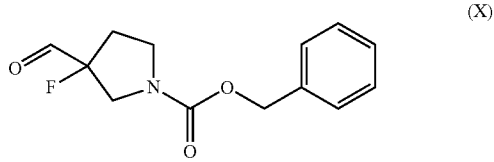 [SMILES: O=CC1(F)CCN(C(=O)OCc2ccccc2)C1]

(X)

This compound of structural formula (X) may then be reacted, which may be without isolation of the compound of formula (X), with an ylide of structural formula (XI):

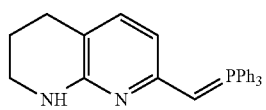

to thereby form the compound of formula (VIII) which exists as a mixture of geometrical isomers (E) and (Z). It will be appreciated by those skilled in the art that there are other methods for forming compound of formula (VIII) from the aldehyde (X). The geometrical isomers can be separated by chromatography or used in the next step as a mixture. This overall scheme for preparation of compounds of structural formula (I) is summarised below as Scheme (I):

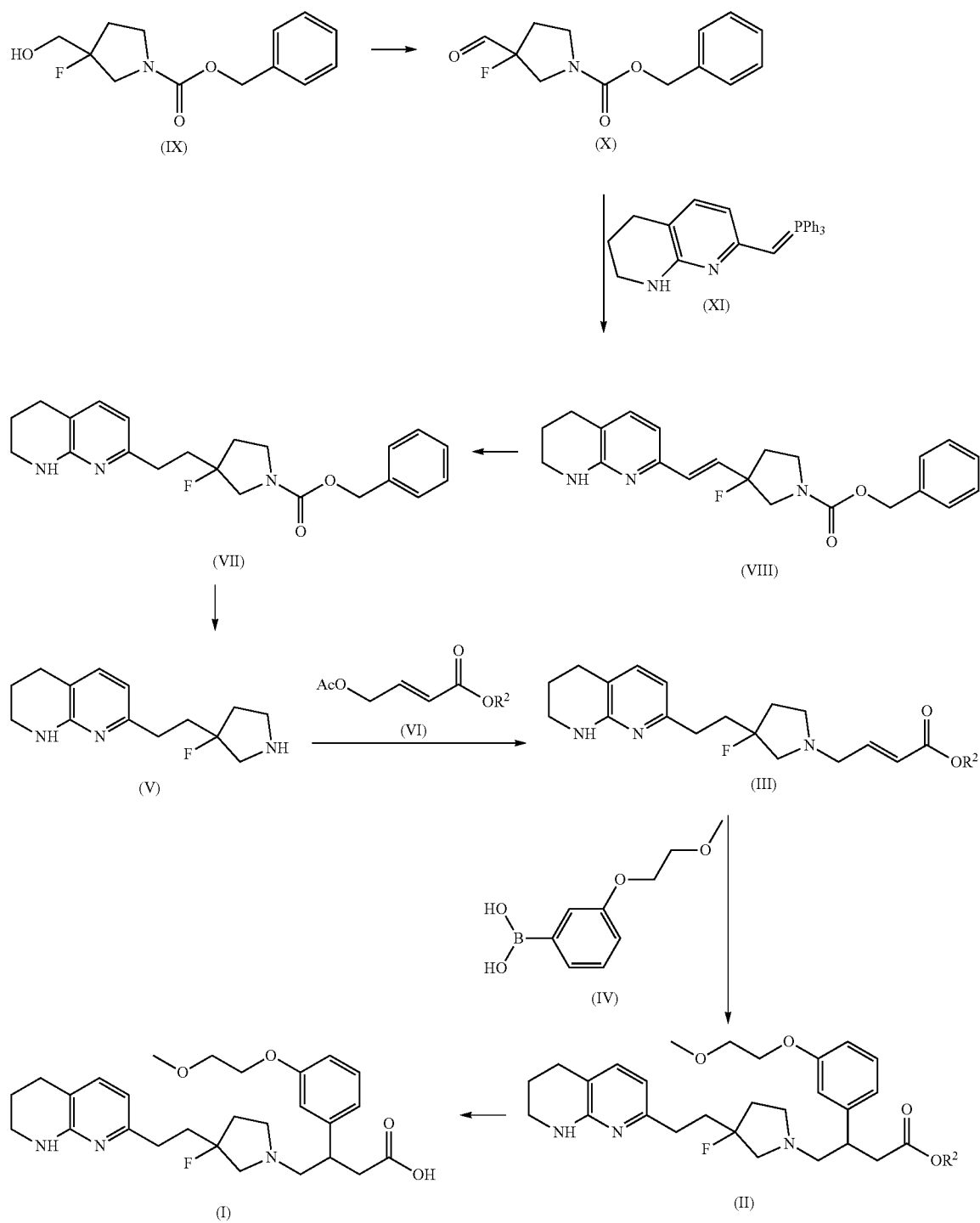

Ylide of structural formula (XI) may be made starting from compound of formula (XII) (available from Fluorochem):

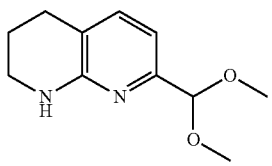
(XII)

which by reaction with first hydrochloric acid followed by neutralisation with sodium bicarbonate may then be converted into an aldehyde of structural formula (XIII):

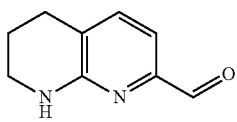
(XIII)

which may be reduced e.g. using sodium borohydride to the corresponding alcohol of structural formula (XIV):

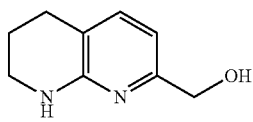
(XIV)

(See also the routes disclosed in US-A-20040092538 for preparation of alcohols of formula (XIV).) which may then be brominated e.g. using phosphorus tribromide to produce the corresponding bromo compound of structural formula (XV):

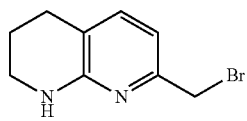
(XV)

which may be converted to the triphenylphosphonium bromide (XVI) by reacting with triphenylphosphine in a solvent such as acetonitrile.

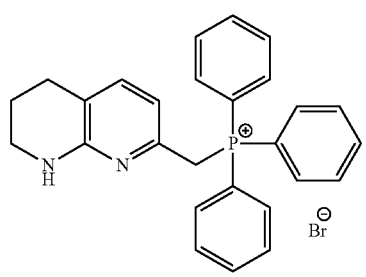
(XVI)

The above-mentioned ylide compound of structural formula (XI) may be obtained by reaction of compound of structural formula (XVI) with a base, such as a solution of potassium tert-butoxide in an inert solvent, such as THF. The ylide of structural formula (XI) may be isolated or preferably formed in situ and reacted in the same vessel with an aldehyde of structural formula (X) without prior isolation.

This overall scheme for preparation of ylide of structural formula (XI) is summarised below as Scheme (II):

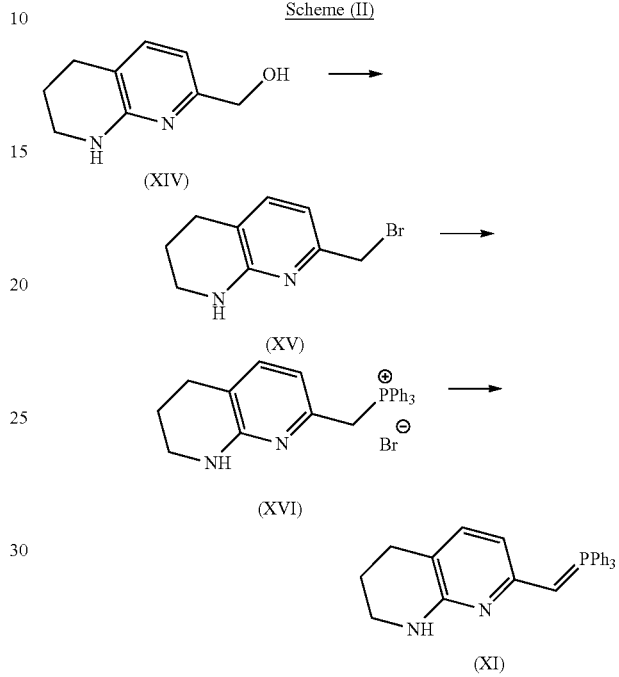

Scheme (II)

Each of the two commercially available enantiomers of compound of formula (IX) provides one major diastereoisomer of compound of formula (I) which is more potent than the corresponding minor one.

It will be appreciated that in any of the routes described above it may be advantageous to protect one or more functional groups. Examples of protecting groups and the means for their removal can be found in T. W. Greene 'Protective Groups in Organic Synthesis' (3rd edition, J. Wiley and Sons, 1999). Suitable amine protecting groups include acyl (e.g. acetyl), carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Compounds of formulae (III), (V) to (VIII), (X), (XI), (XV) and (XVI) are also believed to be novel and therefore form a yet further aspect of the invention The absolute configuration of compounds of formula (I) may be obtained following an independent enantioselective synthesis from an intermediate of known absolute configuration.

Alternatively an enantiomerically pure compound of formula (I) may be converted into a compound whose absolute configuration is known. In either case comparison of spectroscopic data, optical rotation and retention times on an analytical HPLC column may be used to confirm absolute configuration. A third option where feasible is determination of absolute configuration through X-Ray crystallography.

Methods of Use

The compounds of formula (I) and salts thereof are believed to have $\alpha_v$ integrin antagonist activity, particularly $\alpha_v\beta_6$ receptor activity, and thus have potential utility in the treatment of diseases or conditions for which an $\alpha_v\beta_6$ antagonist is indicated.

The present invention thus provides a compound of formula (I) or a pharmaceutically acceptable salt thereof for use in therapy. The compound of formula (I) or pharmaceutically acceptable salt thereof can be for use in the treatment of a disease or condition for which an $\alpha_v\beta_6$ integrin antagonist is indicated.

The present invention thus provides a compound of formula (I) or a pharmaceutically acceptable salt thereof for use in the treatment of a disease or condition for which an $\alpha_v\beta_6$ integrin antagonist is indicated.

Also provided is the use of a compound of formula (I) or a pharmaceutically acceptable salt thereof in the manufacture of a medicament for the treatment of a disease or condition for which an $\alpha_v\beta_6$ integrin antagonist is indicated.

Also provided is a method of treating a disease or conditions for which an $\alpha_v\beta_6$ integrin antagonist is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Fibrotic diseases involve the formation of excess fibrous connective tissue in an organ or tissue in a reparative or reactive process. $\alpha_v\beta_6$ antagonists are believed to be useful in the treatment of a variety of such diseases or conditions including those dependent on $\alpha_v\beta_6$ integrin function and on activation of transforming growth factor beta via alpha v integrins. Diseases may include but are not limited to pulmonary fibrosis (e.g. idiopathic pulmonary fibrosis, non-specific interstitial pneumonia (NSIP), usual interstitial pneumonia (UIP), Hermansky-Pudlak syndrome, progressive massive fibrosis (a complication of coal workers' pneumoconiosis), connective tissue disease-related pulmonary fibrosis, airway fibrosis in asthma and COPD, ARDS associated fibrosis, acute lung injury, radiation-induced fibrosis, familial pulmonary fibrosis, pulmonary hypertension); renal fibrosis (diabetic nephropathy, IgA nephropathy, lupus nephritis, focal segmental glomerulosclerosis (FSGS), transplant nephropathy, autoimmune nephropathy, drug-induced nephropathy, hypertension-related nephropathy, nephrogenic systemic fibrosis); liver fibrosis (virally-induced fibrosis (e.g. hepatitis C or B), autoimmune hepatitis, primary biliary cirrhosis, alcoholic liver disease, non-alcoholic fatty liver disease including non-alcoholic steatohepatitis (NASH), congenital hepatic fibrosis, primary sclerosing cholangitis, drug-induced hepatitis, hepatic cirrhosis); skin fibrosis (hypertrophic scars, scleroderma, keloids, dermatomyositis, eosinophilic fasciitis, Dupytrens contracture, Ehlers-Danlos syndrome, Peyronie's disease, epidermolysis bullosa dystrophica, oral submucous fibrosis); ocular fibrosis (age-related macular degeneration (AMD), diabetic macular oedema, dry eye, glaucoma) corneal scarring, corneal injury and corneal wound healing, prevention of filter bleb scarring post trabeculectomy surgery; cardiac fibrosis (congestive heart failure, atherosclerosis, myocardial infarction, endomyocardial fibrosis, hypertrophic cardiomyopathy (HCM)) and other miscellaneous fibrotic conditions (mediastinal fibrosis, myelofibrosis, retroperitoneal fibrosis, Crohn's disease, neurofibromatosis, uterine leiomyomas (fibroids), chronic organ transplant rejection. There may be additional benefits for additional inhibition of $\alpha_v\beta_1$, $\alpha_v\beta_5$ or $\alpha_v\beta_8$ integrins In addition, pre-cancerous lesions or cancers associated with $\alpha_v\beta_6$ integrins may also be treated (these may include but are not limited to endometrial, basal cell, liver, colon, cervical, oral, pancreas, breast and ovarian cancers, Kaposi's sarcoma, Giant cell tumours and cancer associated stroma). Conditions that may derive benefit from effects on angiogenesis may also benefit (e.g. solid tumours).

The term "disease or condition for which an $\alpha_v\beta_6$ antagonist is indicated", is intended to include any or all of the above disease states.

In one embodiment the disease or condition for which an $\alpha_v\beta_6$ antagonist is indicated is idiopathic pulmonary fibrosis.

In another embodiment the disease or condition for which an $\alpha_v\beta_6$ antagonist is indicated is selected from corneal scarring, corneal injury and corneal wound healing.

Compositions

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts are as described above. The carrier(s), diluent(s) or excipient(s) must be acceptable in the sense of being compatible with the other ingredients of the composition and not deleterious to the recipient thereof.

In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Further provided is a pharmaceutical composition for the treatment of diseases or conditions for which an $\alpha_v\beta_6$ integrin antagonist is indicated comprising a compound of formula (I) or a pharmaceutically acceptable salt thereof.

Further provided is a pharmaceutical composition comprising 0.01 to 3000 mg of a compound of formula (I) or a pharmaceutical salt thereof and 0.1 to 2 g of one or more pharmaceutically acceptable carriers, diluents or excipients.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vagina, ocular or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for oral administration.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine particle size (e.g. by micronisation) and mixing with a similarly prepared pharmaceutical carrier such as an edible carbohydrate, as, for example, starch or mannitol. Flavouring, preservative, dispersing and colouring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilising agent such as agaragar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like.

Lubricants used in these dosage forms include sodium oleate, sodium stearate, magnesium stearate, sodium benzoate, sodium acetate, sodium chloride and the like.

Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water miscible ointment base. Alternatively, the active ingredient may be formulated in a cream with an oil-in-water cream base or a water-in-oil base. The compounds of this invention can be administered as topical eye drops. The compounds of this invention can be administered via sub-conjunctival, intracameral or intravitreal routes which would necessitate administration intervals that are longer than daily.

Pharmaceutical formulations adapted for topical administrations to the eye include eye drops wherein the active ingredient is dissolved or suspended in a suitable carrier, especially an aqueous solvent. Formulations to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Formulations for drug delivery using ocular devices may combine one or more active agents and adjuvants appropriate for the indicated route of administration. For example, the active agents may be admixed with any pharmaceutically acceptable excipient, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, tableted or encapsulated for conventional administration. Alternatively, the compounds may be dissolved in polyethylene glycol, propylene glycol, carboxymethyl cellulose colloidal solutions, ethanol, corn oil, peanut oil, cottonseed oil, sesame oil, tragacanth gum, and/or various buffers. The compounds may also be mixed with compositions of both biodegradable and non-biodegradable polymers and a carrier or diluent that has a time delay property. Representative examples of biodegradable compositions can include albumin, gelatin, starch, cellulose, dextrans, polysaccharides, poly (D, L-lactide), poly (D, L-lactide-co-glycolide), poly (glycolide), poly (hydroxybutyrate), poly (alkylcarbonate) and poly (orthoesters) and mixtures thereof. Representative examples of non-biodegradable polymers can include EVA copolymers, silicone rubber and poly (methylacrylate), and mixtures thereof.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions, gels or dry powders.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. The compositions may be presented in unitdose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for sub-cutaneous or intramuscular administration include poly(lactic-co-glycolic acid) (PLGA) copolymer to form microparticles containing the active pharmaceutical ingredient to provide sustain release.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.1 to 2000 mg, of a compound of the invention calculated as the zwitterion parent compound.

The pharmaceutically acceptable compounds of the invention can be administered in a daily dose (for an adult patient) of, for example, an oral or parenteral dose of 0.01 mg to 3000 mg per day or 0.5 to 1000 mg per day of the compound of the formula (I) or a pharmaceutically acceptable salt thereof, calculated as the zwitterion. This amount may be given in a single dose per day or more usually in a number (such as two, three, four, five or six) of sub-doses per day such that the total daily dose is the same. An effective amount of a salt thereof may be determined as a proportion of the effective amount of the compound of formula (I) per se.

The compounds of the invention may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of the invention and the other pharmaceutically active agent(s) may be administered together in a single pharmaceutical composition or separately and, when administered separately this may occur simultaneously or sequentially in any order. The amounts of the compound(s) of the invention and the other pharmaceutically active agent(s) and the relative timings of administration will be selected in order to achieve the desired combined therapeutic effect.

Thus in a further aspect, there is provided a combination comprising a compound of the invention and at least one other pharmaceutically active agent.

Thus in one aspect, the compound and pharmaceutical compositions according to the invention may be used in combination with or include one or more other therapeutic agents, including therapies for allergic disease, inflammatory disease, autoimmune disease, anti-fibrotic therapies and therapies for obstructive airway disease, therapies for diabetic ocular diseases, and therapies for corneal scarring, corneal injury and corneal wound healing.

Anti-allergic therapies include antigen immunotherapy (such as components and fragments of bee venom, pollen, milk, peanut, CpG motifs, collagen, other components of extracellular matrix which may be administered as oral or sublingual antigens), anti-histamines (such as cetirizine, loratidine, acrivastine, fexofenidine, chlorphenamine), and corticosteroids (such as fluticasone propionate, fluticasone furoate, beclomethasone dipropionate, budesonide, ciclesonide, mometasone furoate, triamcinolone, flunisolide, prednisolone, hydrocortisone).

Anti-inflammatory therapies include NSAIDs (such as aspirin, ibuprofen, naproxen), leukotriene modulators (such as montelukast, zafirlukast, pranlukast), and other anti-inflammatory therapies (such as iNOS inhibitors, tryptase inhibitors, IKK2 inhibitors, p38 inhibitors (losmapimod, dilmapimod), elastase inhibitors, beta2 agonists, DP1 antagonists, DP2 antagonists, pI3K delta inhibitors, ITK inhibitors, LP (lysophosphatidic) inhibitors or FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); adenosine a2a agonists (such as adenosine and regadenoson), chemokine antagonists (such as CCR3 antagonists or CCR4 antagonists), mediator release inhibitors.

Therapies for autoimmune disease include DMARDS (such as methotrexate, leflunomide, azathioprine), biopharmaceutical therapies (such as anti-IgE, anti-TNF, anti-interleukins (such as anti-IL-1, anti-IL-6, anti-IL-12, anti-IL-17, anti-IL-18)), receptor therapies (such as etanercept and similar agents); antigen non-specific immunotherapies (such as interferon or other cytokines/chemokines, cytokine/ chemokine receptor modulators, cytokine agonists or antagonists, TLR agonists and similar agents).

Other anti-fibrotic therapies includes inhibitors of TGFβ synthesis (such as pirfenidone), tyrosine kinase inhibitors targeting the vascular endothelial growth factor (VEGF), platelet-derived growth factor (PDGF) and fibroblast growth factor (FGF) receptor kinases (such as Nintedanib (BIBF-1120) and imatinib mesylate (Gleevec)), endothelin receptor antagonists (such as ambrisentan or macitentan), antioxidants (such as N-acetylcysteine (NAC); broad-spectrum antibiotics (such as cotrimoxazole, tetracyclines (minocycline hydrochloride)), phosphodiesterase 5 (PDE5) inhibitors (such as sildenafil), anti-αvβx antibodies and drugs (such as anti-αvβ6 monoclonal antibodies (such as those described in WO2003100033A2); intetumumab; cilengitide) may be used in combination.

Therapies for obstructive airway diseases include bronchodilators such as short-acting β2-agonists, such as salbutamol), long-acting β2-agonists (such as salmeterol, formoterol and vilanterol), short-acting muscarinic antagonists (such as ipratropium bromide), long-acting muscarinic antagonists, (such as tiotropium, umeclidinium).

In some embodiments, treatment can also involve combination of a compound of this invention with other existing modes of treatment, for example existing agents for treatment of diabetic ocular diseases, such as anti VEGF therapeutics e.g. Lucentis®, Avastin®, and Aflibercept® and steroids, e.g., triamcinolone, and steroid implants containing fluocinolone acetonide.

In some embodiments, treatment can also involve combination of a compound of this invention with other existing modes of treatment, for example existing agents for treatment of corneal scarring, corneal injury or corneal wound healing, such as Gentel®, calf blood extract, Levofloxacin®, and Ofloxacin®.

The compounds and compositions of the present invention may be used to treat cancers alone or in combination with cancer therapies including chemotherapy, radiotherapy, targeted agents, immunotherapy and cell or gene therapy.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

It will be appreciated that when the compound of the present invention is administered in combination with one or more other therapeutically active agents normally administered by the inhaled, intravenous, oral, intranasal, ocular topical or other route that the resultant pharmaceutical composition may be administered by the same route. Alternatively, the individual components of the composition may be administered by different routes.

The present inventions will now be illustrated by way of example only.

Abbreviations

The following list provides definitions of certain abbreviations as used herein. It will be appreciated that the list is not exhaustive, but the meaning of those abbreviations not herein below defined will be readily apparent to those skilled in the art.

Ac (acetyl)
BCECF-AM (2',7'-bis-(2-carboxyethyl)-5-(and-6)-carboxy-fluorescein acetoxymethyl ester)
BEH (Ethylene Bridged Hybrid Technology)
Bu (butyl)
CBZ (carboxybenzyl)
CHAPS (3-[(3-Cholamidopropyl)dimethylammonio]-1-propanesulfonate)
Chiralcel OD-H (cellulose tris(3,5-dimethylphenylcarbamate) coated on 5·m silica gel)
Chiralpak AD-H (amylose tris(3,5-dimethylphenylcarbamate) coated on 5·m silica gel)
Chiralpak ID (amylose tris(3-chlorophenylcarbamate) immobilised on 5·m silica gel)
Chiralpak AS (amylose tris((5)-alpha-methylbenzylcarbamate) coated on 5·m silica gel)
CDI (carbonyl diimidazole)
CSH (Charged Surface Hybrid Technology)
CV (column volume)
DCM (dichloromethane)
DIPEA (diisopropylethylamine)
DMF (N,N-dimethylformamide)
DMSO (dimethylsulfoxide)
DSC (differential scanning colorimetry)
Et (ethyl)
EtOH (ethanol)
EtOAc (ethyl acetate)
h (hour/hours)
HCl (Hydrochloric acid)
HEPES (4-(2-hydroxyethyl)-1-piperazineethanesulfonic acid)
LCMS (liquid chromatography mass spectrometry)
MDAP (mass directed auto-preparative HPLC)
MDCK (Madin-Darby canine kidney)
Me (methyl)
MeCN (acetonitrile)
MeOH (methanol)
MS (mass spectrum)
min minute/minutes
$PdCl_2$(dppf)-$CH_2Cl_2$ [1,1'-Bis(diphenylphosphino)ferrocene]dichloropalladium(II), complex with dichloromethane
Ph (phenyl)
$^i$Pr (isopropyl)
(R)-BINAP (R)-(+)-2,2'-bis(diphenylphosphino)-1,1'-binaphthalene
[Rh(COD)Cl]$_2$ ((chloro(1,5-cyclooctadiene)rhodium(I) dimer)
RT (Retention Time)
SPE (solid phase extraction)
TBME (tert-butyl methyl ether)
TEA (triethylamine)
TFA (trifluoroacetic acid)
TGA (thermal gravimetric analysis)
THF (tetra hydrofuran)
TLC (thin layer chromatography)
UPLC (Ultra Performance Liquid Chromatography)

All references to brine refer to a saturated aqueous solution of sodium chloride.

EXPERIMENTAL DETAILS

Analytical LCMS

Analytical LCMS was conducted on one of the following systems A, B or C.

The UV detection to all systems was an averaged signal from wavelength of 220 nm to 350 nm and mass spectra were recorded on a mass spectrometer using alternate-scan positive and negative mode electrospray ionization.

Experimental details of LCMS systems A-D as referred to herein are as follows:

System A
Column: 50 mm×2.1 mm ID, 1.7 μm Acquity UPLC BEH $C_{18}$ column
Flow Rate: 1 mL/min.
Temp.: 40° C.
Solvents: A: 10 mM ammonium bicarbonate in water adjusted to pH10 with ammonia solution
B: Acetonitrile

| Gradient: | | |
|---|---|---|
| Time (min) | A % | B % |
| 0 | 99 | 1 |
| 1.5 | 3 | 97 |
| 1.9 | 3 | 97 |
| 2.0 | 99 | 1 |

System B
Column: 50 mm×2.1 mm ID, 1.7 μm Acquity UPLC BEH C18 column
Flow Rate: 1 mL/min
Temp.: 40° C.
Solvents: A: 0.1% v/v solution of formic acid in water
B: 0.1% v/v solution of formic acid in acetonitrile

| Gradient: | | |
|---|---|---|
| Time (min) | A % | B % |
| 0 | 97 | 3 |
| 1.5 | 0 | 100 |
| 1.9 | 0 | 100 |
| 2.0 | 97 | 3 |

System C
Column: 50 mm×2.1 mm ID, 1.7 μm Acquity UPLC CSH C18 column
Flow Rate: 1 mL/min.
Temp.: 40° C.
Solvents: A: 10 mM ammonium bicarbonate in water adjusted to pH10 with ammonia solution
B: Acetonitrile

| Gradient: | | |
|---|---|---|
| Time (min) | A % | B % |
| 0 | 97 | 3 |
| 1.5 | 5 | 95 |
| 1.9 | 5 | 95 |
| 2.0 | 97 | 3 |

System D

Column: 50 mm×2.1 mm ID, 1.7 µm Acquity UPLC BEH C18 column

Flow Rate: 1 mL/min

Temp.: 40° C.

Solvents: A: 0.1% v/v solution of trifluoroacetic acid in water

B: 0.1% v/v solution of trifluoroacetic acid in acetonitrile

| Gradient: | | |
|---|---|---|
| Time (min) | A % | B % |
| 0 | 95 | 5 |
| 1.5 | 5 | 95 |
| 1.9 | 5 | 95 |
| 2.0 | 95 | 5 |

Intermediate 1

7-(Bromomethyl)-1,2,3,4-tetrahydro-1,8-naphthyridine (Compound XV)

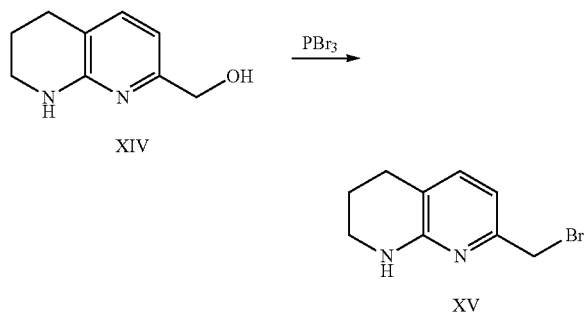

Phosphorus tribromide (0.565 mL, 5.99 mmol) was added dropwise to a suspension of (5,6, 7, 8-tetrahydro-1,8-naphthyridin-2-yl) methanol (Compound XIV)): see US20040092538, page 80) (820 mg, 4.99 mmol) in anhydrous acetonitrile (50 mL) at 0° C. under nitrogen. Upon addition a deep orange coloured precipitate formed, which turned to pale orange. The reaction mixture was stirred at 0° C. for 1 h by which time the reaction was complete. The mixture was concentrated in vacuo and the residue was partitioned between ethyl acetate (250 mL) and a saturated aqueous solution of NaHCO$_3$ (250 mL). The aqueous phase was further extracted with ethyl acetate (250 mL). The combined organic solutions were passed through a hydrophobic frit and then concentrated in vacuo to give the title compound (1.05 g, 93%) as a fluffy creamy solid: LCMS (System C) RT=0.95 min, ES+ve m/z 227, 229 (M+H)$^+$.

Intermediate 2

Triphenyl ((5,6,7,8-tetrahydro-1,8-naphthyridin-2-yl) methyl) phosphonium bromide (Compound (XVI))

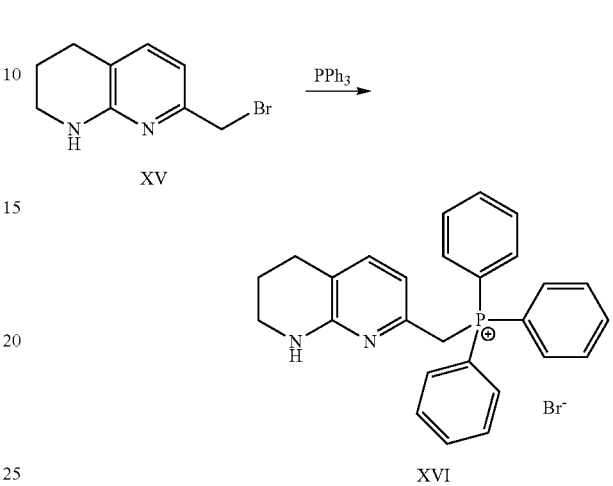

A solution of 7-(bromomethyl)-1,2,3,4-tetrahydro-1,8-naphthyridine (Compound (XV), Intermediate 1) (1.00 g, 4.40 mmol) in acetonitrile (98 mL) was treated with triphenylphosphine (1.270 g, 4.84 mmol) and the solution was stirred at room temperature under nitrogen overnight. The mixture was concentrated in vacuo to give a dark cream solid, which was then triturated with diethyl ether to give the title compound (2.139 g, 99%) as a pale cream solid: LCMS (System C) RT=1.23 min, ES+ve m/z 409 (M+H)$^+$.

Intermediate 3

(E, Z) Benzyl 3-fluoro-3-(2-(5,6,7,8-tetrahydro-1,8-naphthyridin-2-yl) vinyl) pyrrolidine-1-carboxylate, (Compound (VIII)

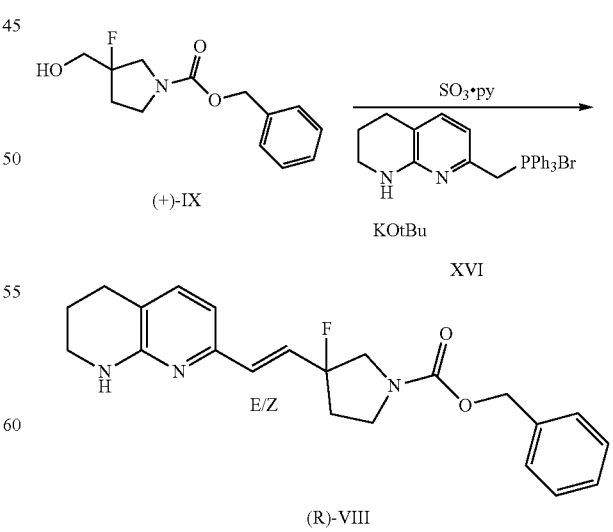

A stirred solution of (+)-benzyl 3-fluoro-3-(hydroxymethyl) pyrrolidine-1-carboxylate (Compound (IX): available from Wuxi App Tec) (260 mg, 1.03 mmol) in DCM (3 mL) and DMSO (0.3 mL), under nitrogen, was treated with DIPEA (0.896 mL, 5.13 mmol). After cooling to 0-5° C. (ice bath) pyridine sulfur trioxide (327 mg, 2.05 mmol) was added portionwise over ca. 5 min to oxidise the alcohol compound (IX) to the corresponding aldehyde compound (X) which was not isolated. The cooling bath was removed and stirring was continued for 0.5 h. Meanwhile a solution of triphenyl ((5, 6, 7, 8-tetrahydro-1, 8-naphthyridin-2-yl) methyl) phosphonium bromide (Compound (XVI), for a preparation see Intermediate 2) (553 mg, 1.13 mmol) in anhydrous DCM (10 mL), under nitrogen, was treated dropwise with potassium tert-butoxide (1M in THF) (1.232 mL, 1.232 mmol) over ca. 5 min resulting in an orange coloured solution. Stirring was continued for 10 min and then the aldehyde (formula (X)) solution was added to the ylide solution in one shot and the mixture was stirred at ambient temperature for 22 h. The reaction mixture was diluted with DCM (20 mL), washed with saturated aqueous sodium bicarbonate (20 mL) and brine (20 mL), dried ($Na_2SO_4$) then evaporated in vacuo. The dark brown residue was purified by chromatography on a 20 g silica SPE cartridge and eluted with a gradient of 0-100% ethyl acetate-cyclohexane over 30 min to obtain the title compound as two geometrical isomers:

Isomer 1: a straw-coloured gum (123.4 mg, 31%), LCMS (System A) RT=1.28 min, 95%, ES+ve m/z 382 (M+H)+ and Isomer 2: a straw-coloured gum (121.5 mg, 31%), LCMS (System A) RT=1.22 min, 91%, ES+ve m/z 382 (M+H)+

Overall yield=244.9 mg, 62.5%.

The configuration of Intermediate 3 was subsequently shown to be (R) and the two geometrical isomers are: (R,E)-benzyl 3-fluoro-3-(2-(5,6,7,8-tetrahydro-1,8-naphthyridin-2-yl)vinyl)pyrrolidine-1-carboxylate and (R,Z)-benzyl 3-fluoro-3-(2-(5,6,7,8-tetrahydro-1,8-naphthyridin-2-yl)vinyl)pyrrolidine-1-carboxylate.

Intermediate 4

Benzyl 3-fluoro-3-(2-(5,6,7,8-tetrahydro-1,8-naphthyridin-2-yl)ethyl)pyrrolidine-1-carboxylate (Compound (VII))

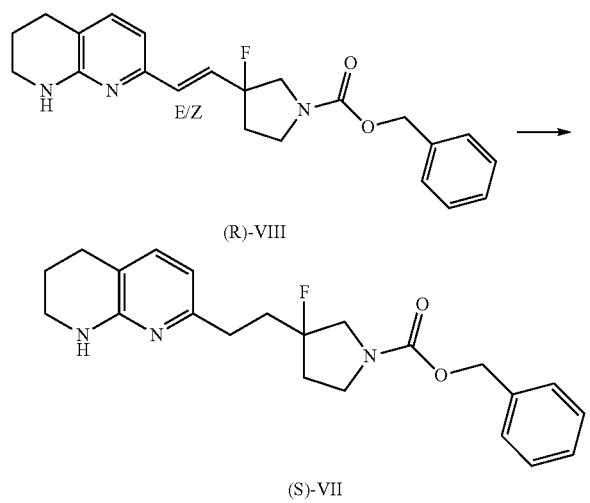

A solution of (E,Z)-benzyl 3-fluoro-3-(2-(5,6,7,8-tetrahydro-1,8-naphthyridin-2-yl)vinyl)pyrrolidine-1-carboxylate (Compound VIII, Intermediate 3) (244 mg, 0.640 mmol) (1:1, E:Z) in DMF (2 mL) was treated with benzenesulfonyl hydrazide (available from Alfa Aesar) (275 mg, 1.60 mmol) and potassium carbonate (354 mg, 2.56 mmol). The reaction mixture was heated to 130° C. for 1 h, then allowed to cool and partitioned between DCM and water. The organic phase was washed with water and dried through a hydrophobic frit. The organic solution was evaporated in vacuo and the residual orange oil was purified by chromatography on a silica cartridge (20 g) eluting with a gradient of 0-50% [(3:1 EtOAc-EtOH)-EtOAc] over 20 min. The appropriate fractions were combined and evaporated in vacuo to give the title compound (150 mg, 61%) as a pale yellow gum: LCMS (System A) RT=1.24 min, 90%, ES+ve m/z 384 (M+H)+. The absolute configuration of Intermediate 4 was subsequently shown to be (S) hence the compound is (S)-benzyl 3-fluoro-3-(2-(5,6,7,8-tetrahydro-1,8-naphthyridin-2-yl) ethyl)pyrrolidine-1-carboxylate. The change from (R) in Intermediate 3 to (S) in Intermediate 4 is due to the change in priority on removal of the double bond.

Intermediate 5

7-(2-(3-Fluoropyrrolidin-3-yl)ethyl)-1,2,3,4-tetrahydro-1,8-naphthyridine (Compound (V))

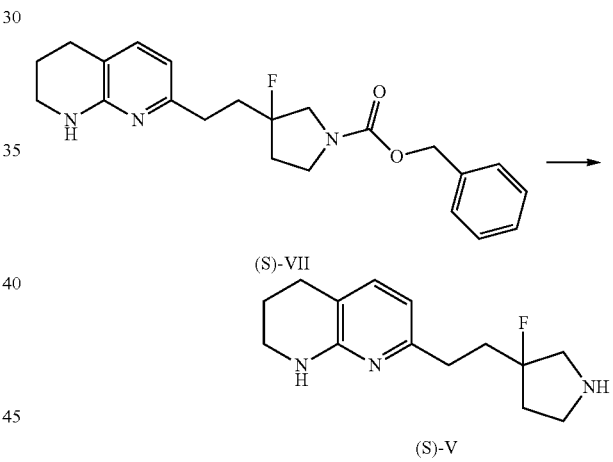

A stirred solution of benzyl 3-fluoro-3-(2-(5,6,7,8-tetrahydro-1,8-naphthyridin-2-yl)ethyl)pyrrolidine-1-carboxylate (Compound (VII, Intermediate 4) (4.67 g, 12.2 mmol) in ethanol (70 mL) containing 10% palladium on carbon (0.50 g) was stirred under a hydrogen atmosphere for 7 h. LCMS showed incomplete deprotection and additional 10% palladium on carbon (0.25 g) was added and the mixture was stirred under a hydrogen atmosphere overnight. The reaction mixture existed as a dark grey suspension so DCM was added to dissolve up the material until the mixture became black. The catalyst was removed by filtration through a pad of celite and the filtrate and washings were evaporated in vacuo. The residue was evaporated from DCM to obtain the title compound as an orange oil (3.28 g): LCMS (System A) RT=0.79 min, 90%, ES+ve m/z 250 (M+H)+. The configuration of Intermediate 5 was subsequently established as (S) and the name of the compound is (S)-7-(2-(3-fluoropyrrolidin-3-yl)ethyl)-1,2,3,4-tetrahydro-1,8-naphthyridine.

Intermediate 6

[7-(2-(3-Fluoropyrrolidin-3-yl)ethyl)-1,2,3,4-tetrahydro-1,8-naphthyridine, (Compound (V)) methanesulfonic acid salt

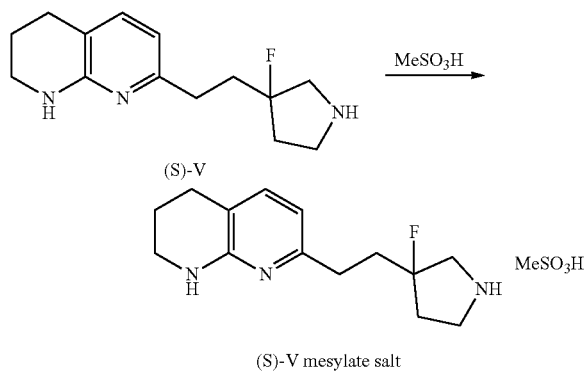

This salt of compound (V) may be prepared and crystallised as a method of purification of compound (V) above.

2-Butanol (5 mL) was added to 7-(2-(3-fluoropyrrolidin-3-yl)ethyl)-1,2,3,4-tetrahydro-1,8-naphthyridine (Compound (V)) (1.0 g, 4.0 mmol) and the mixture was heated until complete dissolution was achieved. Methanesulfonic acid (0.260 mL, 4.01 mmol) was added to the warm solution and the mixture was heated to 80° C. with stirring. The solution was then allowed to cool to ambient temperature. No precipitation was evident immediately, so the solution was cooled further in a fridge (ca. 4° C.). After 3 days, a significant amount of solid was observed. The solid was isolated by filtration and washed with cold 2-butanol, and dried further in vacuo to afford the title compound (600 mg, 43%) as a pale yellow solid: LCMS (System A) RT=0.80 min, 100%, ES+ve m/z 250 (M+H)$^+$; Analytical Chiral HPLC on a Chiralpak AD column (250 mm×4.6 mm) RT=8.41 min, 99.6% and RT=12.03 min, 0.4%, eluting with 40% EtOH-heptane (containing 0.2% isopropylamine), flow rate 1 mL/min, detecting at 235 nm. The configuration of Intermediate 6 was subsequently established as (S) and the name of the compound is (S)-7-(2-(3-fluoropyrrolidin-3-yl)ethyl)-1,2,3,4-tetrahydro-1,8-naphthyridine methanesulfonic acid salt.

Intermediate 7

(E)-Methyl 4-acetoxybut-2-enoate (Compound (VI))

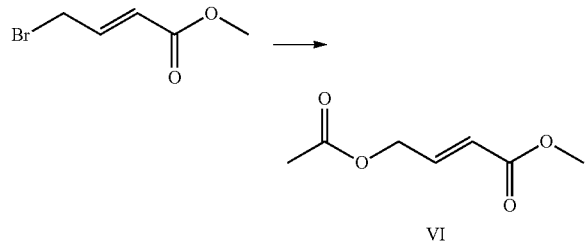

A suspension of sodium acetate (3.5 g, 42 mmol) in MeCN (30 mL) was treated with methyl 4-bromocrotonate (Aldrich) (3.33 mL, 5 g, 28 mmol) and the mixture was heated to 50° C. for 3 d. The mixture was diluted with ether and then filtered. The solid was washed with ether and the combined filtrate and washings was evaporated under reduced pressure. After evaporation the residue was partitioned between ether and water. The organic phase was washed with aqueous sodium bicarbonate, dried over MgSO$_4$, and evaporated under reduced pressure to give a pale orange oil. NMR indicated a mixture of product and starting material, therefore, sodium acetate (3.44 g, 42 mmol) was added to the residual oil, followed by MeCN (10 mL) and the mixture was heated to 70° C. over the weekend. The mixture was concentrated under reduced pressure and the residue was partitioned between ether and water. The organic solution was washed with water, brine, dried (MgSO$_4$) and filtered. The filtrate was evaporated under reduced pressure to give the title compound (3.55 g, 80%) as an orange oil: NMR δ (CDCl$_3$) 6.92 (1H, dt, J 16, 5 Hz), 6.01 (1H, dt, J 16, 2 Hz), 4.72 (2H, dd, J 5, 2 Hz), 3.73 (3H, s), 2.10 (3H, s).

Intermediate 8

(E)-Methyl 4-(3-fluoro-3-(2-(5,6,7,8-tetrahydro-1,8-naphthyridin-2-yl)ethyl)pyrrolidin-1-yl)but-2-enoate (Compound (III))

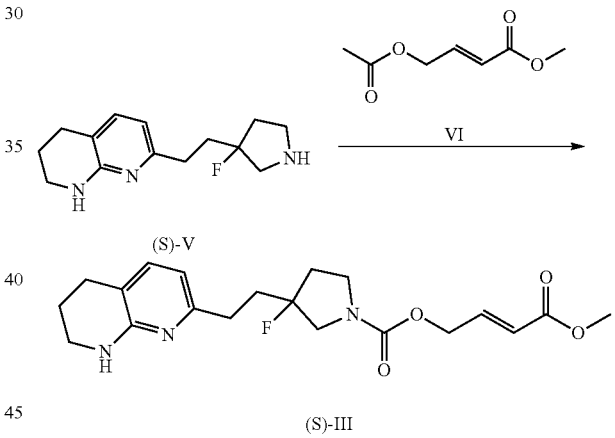

A mixture of (E)-methyl 4-acetoxybut-2-enoate (compound (VI), for a preparation see Intermediate 7) (127 mg, 0.802 mmol), 7-(2-(3-fluoropyrrolidin-3-yl)ethyl)-1,2,3,4-tetrahydro-1,8-naphthyridine (compound (V), for a preparation see Intermediate 5) (200 mg, 0.802 mmol) and PdCl$_2$ (dppf)-CH$_2$Cl$_2$ adduct (65.7 mg, 0.080 mmol) in DCM (2 mL) was stirred at ambient temperature for 2 h. LCMS showed around 50% conversion and DIPEA (0.279 mL, 1.60 mmol) was added and the solution stirred for 2 h at room temperature. LCMS showed almost complete conversion to the product. The material was loaded directly onto a column and purified by chromatography (20 g amino propyl cartridge) eluting with a gradient of 0-100% EtOAc in cyclohexane over 20 min. The appropriate fractions were combined and evaporated to give the title compound (101.4 mg, 36%): LCMS (System A) RT=1.08 min, 95%, ES+ve m/z 348 (M+H)$^+$. The configuration of Intermediate 8 was established as (S) and the name as (S,E)-methyl 4-(3-fluoro-3-(2-(5,6,7,8-tetrahydro-1,8-naphthyridin-2-yl)ethyl)pyrrolidin-1-yl)but-3-enoate.

Intermediate 9

(E, Z) (S)-Benzyl 3-fluoro-3-(2-(5,6,7,8-tetrahydro-1,8-naphthyridin-2-yl) vinyl) pyrrolidine-1-carboxylate, (Compound (XXIII))

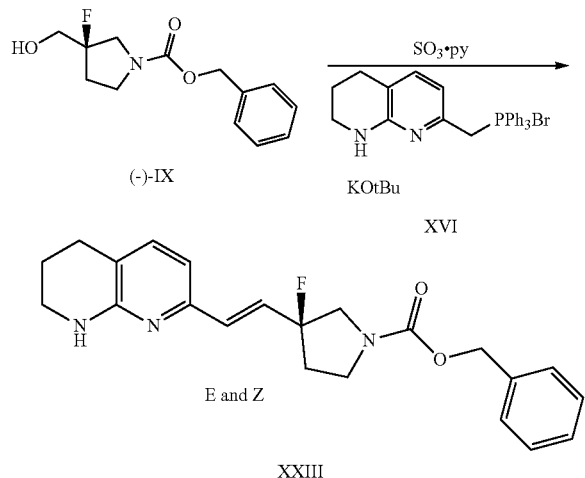

A stirred solution of (R)-(–)-benzyl 3-fluoro-3-(hydroxymethyl)pyrrolidine-1-carboxylate [(–)-compound (IX)] (available from Wuxi App Tec) (4.18 g, 16.50 mmol) in dichloromethane (60 mL) and DMSO (5.86 mL, 83 mmol) was treated with DIPEA (14.41 mL, 83 mmol) under nitrogen. After cooling to 0-5° C. in an ice bath, pyridine sulfur trioxide (5.40 g, 33.9 mmol) was added portion wise over ca. 5 min. The solution turned a pale yellow colour and stirring was continued for ca. 0.5 h to give a yellow solution. The solution was washed with dilute HCl (50 mL) and dried (MgSO₄). Then triphenyl((5,6,7,8-tetrahydro-1,8-naphthyridin-2-yl)methyl)phosphonium bromide (compound XVI, Intermediate 2) (8.06 g, 16.47 mmol) and a small amount of DCM (ca. 5 mL) were added before the addition of cyclohexene (3.81 mL) to give a pale orange solution. Potassium tert-butoxide (19.80 mL, 19.80 mmol) was added dropwise to this solution which resulted in a cream coloured suspension. After 1 h the reaction mixture was diluted with DCM (200 mL), washed with saturated aqueous sodium bicarbonate (200 mL) and brine (200 mL), dried (MgSO₄), then evaporated in vacuo. The dark orange oil solidified overnight and was triturated with diethyl ether (ca. 30 mL), then filtered to give a cream solid and a yellow filtrate. The filtrate was evaporated in vacuo to give an orange oil and this was applied to a 330 g normal phase silica cartridge and eluted with a cyclohexane/ethyl acetate gradient (0-100% ethyl acetate over 50 min). Fractions 16-40 were evaporated in vacuo to give the title compound as a mixture of (E) and (Z) geometrical isomers (3.953 g, 63%) as a straw coloured gum: LCMS (System C) RT=1.28 min, 50% and 1.34 min, 46% ES+ve m/z 382 (M+H)⁺.

Intermediate 10

(R)-Benzyl 3-fluoro-3-(2-(5,6,7,8-tetrahydro-1,8-napthyridin-2-yl)ethyl)pyrrolidine-1-carboxylate

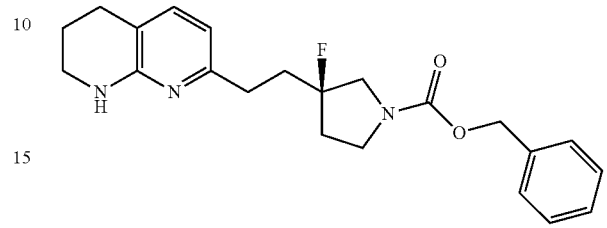

(R)-VII

A stirred solution of (E and Z)-(5)-benzyl 3-fluoro-3-(2-(5,6,7,8-tetrahydro-1,8-naphthyridin-2-yl)vinyl)pyrrolidine-1-carboxylate (Intermediate 9) (3.814 g, 10.00 mmol) in DMF (40 mL) was treated under nitrogen with potassium carbonate (5.53 g, 40.0 mmol), followed by benzenesulfonohydrazide (4.38 g, 25.4 mmol) to give a yellow liquid. The mixture was heated at 100° C. for 1 h, then allowed to cool to ambient temperature and filtered through celite. The filtrate was evaporated in vacuo to give a cream coloured slurry. This was partitioned between water (100 mL) and ethyl acetate (100 mL) and the organic layer further washed with water (4×100 mL), dried (MgSO₄), and then evaporated in vacuo to obtain a yellow oil (3.261 g). This was left on high vacuum line over the weekend (2.982 g). The oil was dissolved in the minimum of DMSO (ca. 3 mL) and applied to a 120 g reverse phase cartridge and eluted with a gradient of 10-100% (acetonitrile containing 0.1% NH₃) in 10 mM aqueous ammonium bicarbonate over 12 CV. Fractions 6-9 were partially evaporated in vacuo to remove the acetonitrile. The remaining solution was diluted with water (40 mL) and DCM (60 mL), then separated. The aqueous layer was further extracted with DCM (3×30 mL) and the organic extracts were combined, dried (MgSO₄) and then evaporated in vacuo to give the title compound (2.145 g, 56%) as a pale yellow oil: LCMS (System C): RT=1.25 min, ES+ve m/z 384 (M+H)⁺.

Intermediate 11

(R)-7-(2-(3-fluoropyrrolidin-3-yl)ethyl)-1,2,3,4-tetrahydro-1,8-naphthyridine

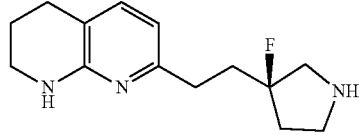

(R)-V

A solution of (R)-benzyl 3-fluoro-3-(2-(5,6,7,8-tetrahydro-1,8-naphthyridin-2-yl)ethyl)pyrrolidine-1-carboxylate (Intermediate 10) (2.334 g, 6.09 mmol) in ethanol (50 mL) was added to 10% Palladium on carbon (250 mg, 0.235 mmol) and the mixture stirred under a hydrogen atmosphere for 3 h at which point more palladium on carbon (107.2 mg) was added. The reaction was stirred overnight. DCM (ca. 30 mL) was added and the mixture filtered through celite under nitrogen. The filtrate was evaporated in vacuo to give the title compound (1.575 g) as a yellow oil: LCMS (System C) RT=0.83 min, ES+ve m/z 250 (M+H)+.

Intermediate 12

(R,E)-Methyl 4-(3-fluoro-3-(2-(5,6,7,8-tetrahydro-1,8-naphthyridin-2-yl)ethyl)pyrrolidin-1-yl)but-2-enoate

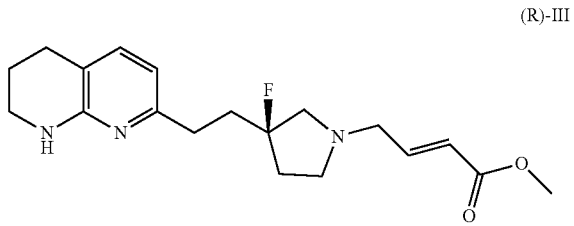 [SMILES: COC(=O)/C=C/CN1CC[C@](F)(CCc2ccc3c(n2)NCCC3)C1]

(R)-III (E)-methyl 4-acetoxybut-2-enoate (Intermediate 7, compound VI) (0.951 g, 6.01 mmol), (R)-7-(2-(3-fluoropyrrolidin-3-yl)ethyl)-1,2,3,4-tetrahydro-1,8-naphthyridine (Intermediate 11) (1.520 g, 6.10 mmol), PdCl$_2$(dppf)-CH$_2$Cl$_2$ adduct (0.242 g, 0.331 mmol) and potassium acetate (2.083 g, 21.22 mmol) were dissolved in DCM (25 mL) and the reaction mixture was stirred under nitrogen for 20 h to give an orange liquid (2.188 g). The reaction mixture was partitioned between DCM (50 mL) and water (50 mL) and extracted once more with DCM (50 mL). The combined organic phases were washed with brine (50 mL) and dried over MgSO$_4$. The solvent was removed in vacuo and the residue was dissolved in DCM and purified on an aminopropyl cartridge (50 g) using a gradient of 0-100% ethyl acetate-cyclohexane over 20 min. The appropriate fractions were combined and evaporated in vacuo to give the title compound (1.59 g, 75%) as a yellow oil. LCMS (System C): RT=1.07 min, ES+ve m/z 348 (M+H)+.

Intermediate 13

Methyl 4-((R)-3-fluoro-3-(2-(5,6,7,8-tetrahydro-1,8-napthyridin-2-yl)ethyl)pyrrolidin-1-yl)-3-(3-(2-methoxyethoxy)phenyl)butanoate

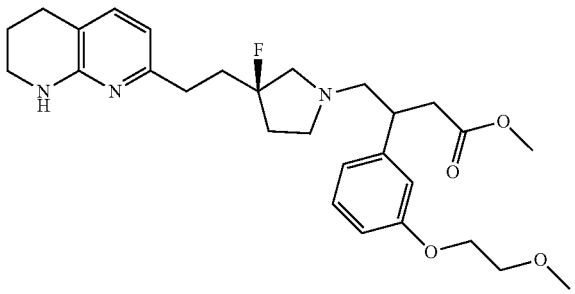

II

A suspension of (R,E)-methyl 4-(3-fluoro-3-(2-(5,6,7,8-tetrahydro-1,8-naphthyridin-2-yl)ethyl)pyrrolidin-1-yl)but-2-enoate (Intermediate 12, compound (R)-III) (0.8 g, 2.303 mmol), (3-(2-methoxyethoxy)phenyl)boronic acid (available from Manchester Organics, Enamine or Combi-Blocks) (1.389 g, 7.09 mmol) and chloro(1,5-cyclooctadiene)rhodium(I) dimer (57 mg, 0.115 mmol) in 1,4-dioxane (10 mL) was degassed. A solution of (R)-BINAP (0.173 g, 0.278 mmol) and 3.8M potassium hydroxide (1.515 mL, 5.76 mmol) in 1,4-dioxane (3.33 mL) was degassed. The latter solution was added to the former solution and the mixture was stirred at 90° C. under nitrogen for 1.5 h. The reaction mixture was allowed to cool and then partitioned between TBME (50 mL) and 2M hydrochloric acid (30 mL). The aqueous phase was basified with saturated sodium bicarbonate solution and then extracted using ethyl acetate (3×30 mL). The ethyl acetate extracts were washed with brine and dried (MgSO$_4$). The solvent was removed in vacuo and the residue was dissolved in the minimum of DCM loaded onto an aminopropyl cartridge (50 g) and chromatographed eluting with a gradient of 0-50% ethyl acetate-cyclohexane over 20 mins. The appropriate fractions were combined and evaporated in vacuo to give the title compound as a mixture of diastereoisomers (0.7 g; ratio 86:14) as a pale yellow oil: LCMS (System C) RT=1.29 min, ES+ve m/z 500 (M+H)+.

PREPARATION OF EXAMPLES

Example 1

(S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid and Example 2

(R)-4-((S)-3-Fluoro-3-(2-(5,6,7,8-tetrahydro-1,8-naphthyridin-2-yl)ethyl)pyrrolidin-1-yl)-3-(3-(2-methoxyethoxy)phenyl)butanoic acid Example 1

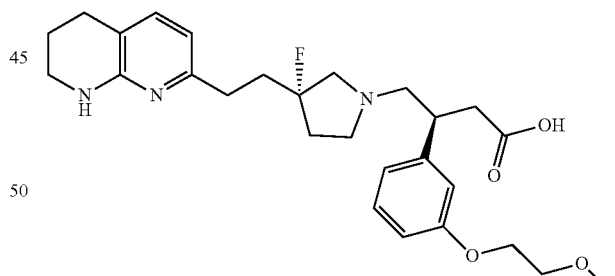

Example 2

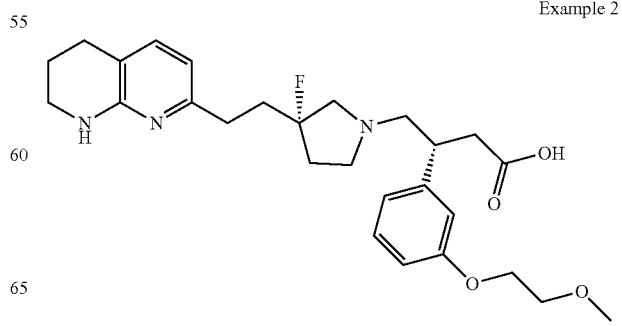

-continued

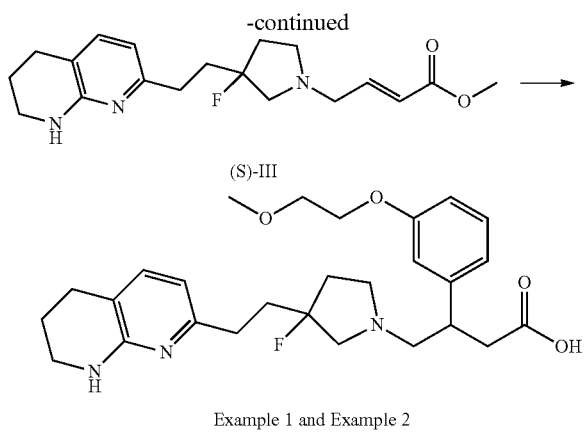

(S)-III

Example 1 and Example 2

(S,E)-Methyl 4-(3-fluoro-3-(2-(5,6,7,8-tetrahydro-1,8-naphthyridin-2-yl)ethyl)pyrrolidin-1-yl)but-2-enoate (Intermediate 8) (101.4 mg, 0.292 mmol), 3.8M KOH (aq) (0.230 mL, 0.876 mmol) and (3-(2-methoxyethoxy)phenyl)boronic acid (compound (IV) from Enamine LLC) (172 mg, 0.876 mmol) were dissolved in 1,4-dioxane (2 mL) and the solution was degassed. [Rh(COD)Cl]$_2$ (7.20 mg, 0.015 mmol) and (R)-BINAP (21.81 mg, 0.035 mmol) were suspended in 1,4-dioxane (2 mL) and degassed. The former solution of the reactants was then added to the latter catalyst solution under nitrogen. The reaction mixture was heated and stirred (50° C. 2 h). The mixture was then loaded onto an SCX cartridge (10 g) (pre-conditioned with 1CV MeOH, 1CV MeCN), washed with 10CV DMSO, 4CV MeCN, and eluted with 2M NH$_3$ in MeOH (4CV). The basic fraction was evaporated under reduced pressure. The residue was dried under high vacuum for 12 h to give (S)-methyl 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoate (Compound (II)) (131.3 mg, 93%).

This methyl ester, Compound (II) was then dissolved in THF (2 mL) and aqueous 1M LiOH (1.459 mL, 1.459 mmol) added. The solution was stirred at room temperature for 18 h. LCMS showed complete hydrolysis to the carboxylic acid and 2M HCl (0.876 mL, 1.751 mmol) was added and the solution was loaded on to a SCX cartridge (10 g) (pre-conditioned with 1CV MeOH, 1CV MeCN), washed with 4CV MeCN, and eluted with 2M NH$_3$ in MeOH (4CV). The basic fraction was evaporated under reduced pressure to give the crude product as a gum (127 mg, 90%). Analytical chiral HPLC RT=9.0 min, 88% and RT=13.8 min, 12% on a Chiralcel OJ-H column (4.6 mm id×25 cm) eluting with 60% EtOH (containing 0.2% isopropylamine)-heptane, flow rate=1.0 mL/min, detecting at 215 nm. The diastereoisomeric mixture of compounds of Formula (I) was separated by preparative chiral HPLC on Chiralcel OJ-H column (3 cm×25 cm) eluting with 60% EtOH-heptane, flow rate=30 mL/min, detecting at 215 nm to give the two individual diastereoisomers of the title compound.

Example 1 (78 mg, 55%): Analytical chiral HPLC RT=9.0 min, 98.7% on a Chiralcel OJ-H column (4.6 mm id×25 cm) eluting with 60% EtOH (containing 0.2% isopropylamine)-heptane, flow rate=1.0 mL/min, detecting at 215 nm; LCMS (System D) RT=0.52 min, 100%, ES+ve m/z 486 (M+H)$^+$ and (System C) RT=0.81 min, 92%, ES+ve m/z 486 (M+H)$^+$ 1H NMR (CDCl$_3$, 600 MHz): δ 8.45 (br s, 1H), 7.21 (t, J=7.7 Hz, 1H), 7.16 (d, J=7.2 Hz, 1H), 6.86-6.73 (m, 3H), 6.31 (d, J=7.2 Hz, 1H), 4.12 (t, J=4.4 Hz, 2H), 4.08 (br s, 1H), 3.75 (td, J=4.7, 0.8 Hz, 2H), 3.73-3.68 (m, 1H), 3.47 (br s, 2H), 3.46 (d, J=1.1 Hz, 2H), 3.42 (br t, J=5.1 Hz, 2H), 3.00-2.85 (m, 2H), 2.82-2.75 (m, 1H), 2.70-2.66 (m, 1H), 2.63-2.57 (m, 1H), 2.73-2.55 (m, 3H), 2.49 (q, J=9.1 Hz, 1H), 2.45 (dd, J=11.9, 3.7 Hz, 1H), 2.23-1.97 (m, 4H), 1.95-1.80 (m, 3H), [α]$_D^{20}$+51 (c=0.72 in ethanol).

The absolute configuration of the asymmetric centres of Example 1 was determined and the compound was found to be (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid (see below).

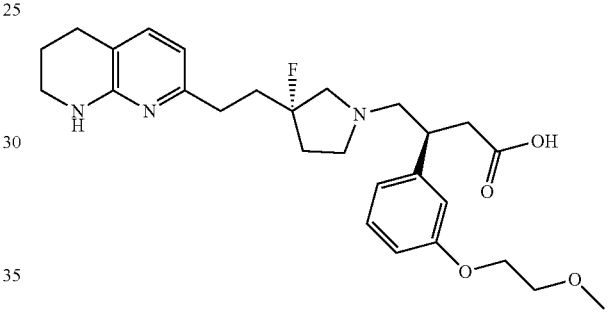

Example 2 (10 mg, 7%): Analytical chiral HPLC RT=12.5 min, >99.5% on a Chiralcel OJ-H column (4.6 mm id×25 cm) eluting with 60% EtOH (containing 0.2% isopropylamine)-heptane, flow rate=1.0 mL/min, detecting at 215 nm; LCMS (SystemC) RT=0.82 min, 84%, ES+ve m/z 486 (M+H)$^+$. [α]$_D^{20}$−28 (c=0.50 in ethanol).

The absolute configuration of the asymmetric centres of Example 2 was determined and the compound was found to be of structural formula (R)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

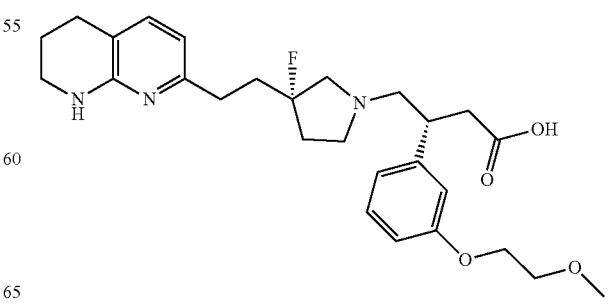

Example 3

(R)-4-((R)-3-Fluoro-3-(2-(5,6,7,8-tetrahydro-1,8-naphthyridin-2-yl)ethyl)pyrrolidin-1-yl)-3-(3-(2-methoxyethoxy)phenyl)butanoic acid and

Example 4

(S)-4-((R)-3-fluoro-3-(2-(5,6,7,8-tetrahydro-1,8-napthyridin-2-yl)ethyl)pyrrolidin-1-yl)-3-(3-(2-methoxyethoxy)phenyl)butanoic acid Example 3

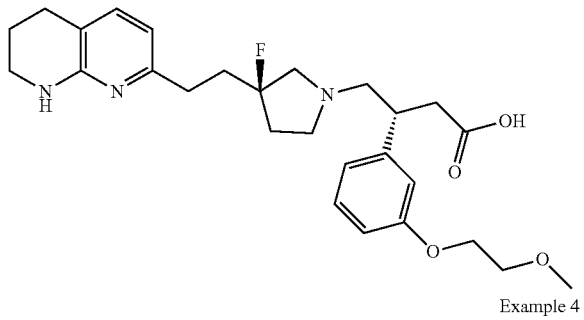

Example 4

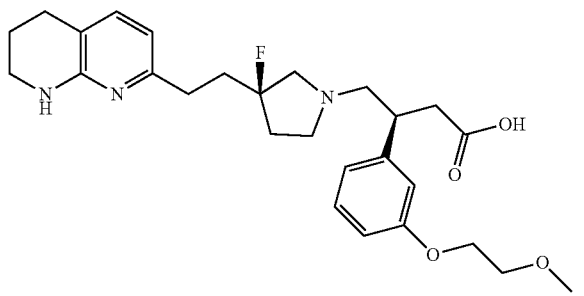 [SMILES: COCCOc1cccc([C@H](CC(=O)O)CN2CC[C@@](F)(CCc3ccc4c(n3)NCCC4)C2)c1]

To a solution of methyl 4-((R)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoate (Intermediate 13) (100 mg, 0.200 mmol) in methanol (1 mL) was added aqueous sodium hydroxide solution (2M, 0.500 mL) and the reaction mixture was stirred at room temperature for 2 h. The reaction mixture was acidified to pH 7 using 2M hydrochloric acid. The solution was diluted with water (10 mL), extracted with ethyl acetate (3×10 mL), the combined organic layers were washed with brine and dried (MgSO$_4$). The solvent was removed in vacuo giving a slightly sticky colourless glass (62 mg, 64%): LCMS (System A) RT=0.8 min, ES+ve m/z 486 (M+H)$^+$. Analytical chiral HPLC RT=7.4 min, 16% and RT=11.8 min, 84% on a Chiralcel OJ column (250 mm×4.6 mm), eluting with 60% EtOH-heptane, flow-rate 1 mL/min, detecting at 215 nm. The diastereoisomers were separated by preparative chiral HPLC on a Chiralcel OJ-H column (250 mm×30 mm) eluting with 50% EtOH in heptane, flow-rate 30 mL/min, to give the two diastereoisomers as Examples 3 and 4.

Example 3 (6 mg, 6%): LCMS (SystemC) RT=0.80 min, 94%, ES+ve m/z 486 (M+H)$^+$; Analytical chiral HPLC RT=7.2 min, >99.5% on a Chiralcel OJ column (250 mm×4.6 mm), eluting with 60% EtOH-heptane, flow-rate 1 mL/min, detecting at 215 nm. (R)-4-((R)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid.

Example 4 (33 mg, 34%): LCMS (SystemC) RT=0.80 min, 100%, ES+ve m/z 486 (M+H)$^+$; Analytical chiral HPLC RT=11.8 min, >99.5% on a Chiralcel OJ column (250 mm×4.6 mm), eluting with 60% EtOH-heptane, flow-rate 1 mL/min, detecting at 215 nm. (S)-4-((R)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid.

Example 5

(S)-4-((S)-3-Fluoro-3-(2-(5,6,7,8-tetrahydro-1,8-naphthyridin-2-yl)ethyl)pyrrolidin-1-yl)-3-(3-(2-methoxyethoxy)phenyl)butanoic acid maleate salt MeCN (100 μL) was added to (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid (Example 1) (112.7 mg) and heated to 60° C. To the solution, maleic acid (solid, ~1 equivalent, 26.82 mg) was added along with seeds of (S)-4-(S)-(3-Fluoro-3-(2-(5,6,7,8-tetrahydro-1,8-naphthyridin-2-yl)ethyl)pyrrolidin-1-yl)-3-(3-morpholinophenyl)butanoic acid maleate salt which is described in our patent application filed on the same day as this present application, and which is hereby incorporated by reference, and the solution was held at 60° C. for 3 h. The solution was cooled step-wise from 60° C. to 5° C. with an hour hold every 5° C. and stirred at 5° C. for ~16 h. The solids were isolated by vacuum filtration and air-dried for 15 min. The yield of crystalline maleate salt was ~41% (57.3 mg).

MeCN (300 μL) was added to (S)-4-((S)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid (Example 1) (298.54 mg) at room temperature. To the solution, maleic acid (solid, ~1 equivalent, 71.05 mg) was added. The suspension was heated to 60° C. to obtain a clear solution. Seeds of maleate salt (obtained above) were added, but the seeds dissolved. The solution was held at 60° C. for an hour and cooled slowly to ~53° C. and re-seeded. The seeds dissolved but slowly. The solution was cooled slowly to 5° C. which led to a thick suspension. To the suspension, di-isopropyl ether (900 μL) was added and stirred at room temperature for two days. The solids were isolated by vacuum filtration, washed with di-isopropyl ether, air-dried for an hour and dried in a vacuum oven at 40° C. overnight. The yield of the crystalline maleate salt was (352.9 mg, 95%).

Example 6

(S)-4-((S)-3-Fluoro-3-(2-(5,6,7,8-tetrahydro-1,8-naphthyridin-2-yl)ethyl)pyrrolidin-1-yl)-3-(3-(2-methoxyethoxy)phenyl)butanoic acid citraconate salt

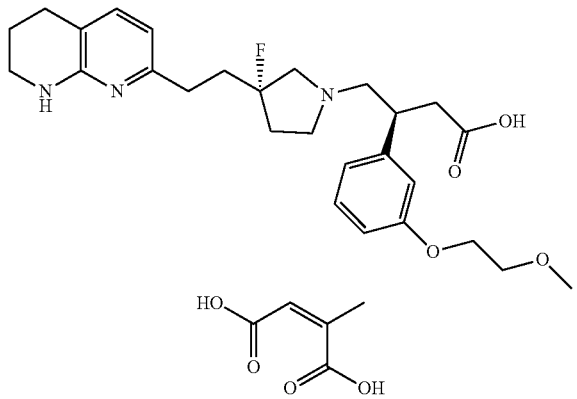

Anhydrous acetonitrile (0.1 mL) was added to (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid (Example 1) (505 mg, 1.04 mmol) which dissolved at ambient temperature. Citraconic acid (28.4 mg, 0.218 mmol) (available from Sigma) was added and suspension heated to 60° C. to obtain a clear yellow solution, then cooled to ~50° C. and held there for 5 min. The solution was cooled to 40° C. and then seeded with the maleate salt (Example 5) without stirring. The mixture was left in the fridge overnight and then treated with diisopropyl ether (0.75 mL)—two layers observed and returned to the fridge (~3 to 4° C.) for 1 h, followed by 1 h in the freezer (−22 to −20° C.) and returned to the fridge for 4 days. Precipitation/crystallisation had occurred and liquid was removed by pipette, and the solid air dried overnight to give the title compound (99 mg, 77%) as a white crystalline solid. $^1$H NMR (600 MHz, $D_2O$) 7.53-7.50 (m, 1H), 7.39-7.35 (m, 1H), 7.01-6.98 (m, 1H), 6.97-6.94 (m, 2H), 6.57-6.55 (m, 1H), 5.84-5.82 (m, 1H), 4.21-4.18 (m, 2H), 3.81-3.79 (m, 2H), 3.77-3.69 (m, 1H), 3.68-3.61 (m, 2H), 3.66-3.57 (m, 2H), 3.52-3.42 (m, 1H), 3.44-3.41 (m, 2H), 3.41 (s, 3H), 3.44-3.40 (m, 1H), 2.87-2.77 (m, 2H), 2.77-2.74 (m, 2H), 2.66-2.61 (m, 1H), 2.57-2.52 (m, 1H), 2.44-2.35 (m, 1H), 2.29-2.17 (m, 1H), 2.28-2.16 (m, 2H), 2.01-1.97 (m, 3H), 1.91-1.86 (m, 2H); Melting point: 103° C. (DSC)

Biological Assays
Cell Adhesion Assays

Reagents and methods utilised were as described [Ludbrook et al, *Biochem. J.* 2003, 369, 311 and Macdonald et al. *ACS Med Chem Lett*, 2014, 5, 1207-1212 for $α_vβ_8$ assay), with the following points of clarification. The following cell lines were used, with ligands in brackets: K562-$α_5β_1$ (Fibronectin), K562-$α_vβ_3$ (LAP-$b_1$), K562-$α_vβ_5$ (Vitronectin), K562-$α_vβ_6$ (LAP-$b_1$), K562-$α_vβ_5$ (LAP-$b_1$). The divalent cation used to facilitate adhesion was 2 mM $MgCl_2$. Adhesion was quantified by cell labelling with the fluorescent dye BCECF-AM (Life Technologies), where cell suspensions at 3×10$^6$ cells/mL were incubated with 0.33 mL/mL of 30 mM BCECF-AM at 37° C. for 10 minutes, then 50 μL/well were dispensed into the 96-well assay plate. At the assay conclusion cells that adhered were lysed using 50 μL/well of 0.5% Triton X-100 in $H_2O$ to release fluorescence. Fluorescence intensity was detected using an Envision® plate reader (Perkin Elmer). For active antagonists in the assay, data were fitted to a 4 parameter logistic equation for $IC_{50}$ determinations.

The affinity ($pIC_{50}$) for Example 1 in the cell Adhesion Assays was for: $α_vβ_6$ $pIC_{50}$=7.9; $α_vβ_3$ $pIC_{50}$=7.4; $α_vβ_5$ $pIC_{50}$=7.4; $α_vβ_8$ $pIC_{50}$=7.5; $α_vβ_1$ $pIC_{50}$=6.4.

The affinity ($pIC_{50}$) for Example 2 in the cell Adhesion Assays was for: $α_vβ_6$ $pIC_{50}$=6.2; $α_vβ_3$ $pIC_{50}$=5.9; $α_vβ_5$ $pIC_{50}$=6.6; $α_vβ_8$ $pIC_{50}$=5.8

The affinity ($pIC_{50}$) for Example 3 in the cell Adhesion Assays was for: $α_vβ_6$ $pIC_{50}$=5.4; $α_vβ_3$ $pIC_{50}$=5.6; $α_vβ_5$ $pIC_{50}$=5.0; $α_vβ_8$ $pIC_{50}$=5.3

The affinity ($pIC_{50}$) for Example 4 in the cell Adhesion Assays was for: $α_vβ_6$ $pIC_{50}$=7.7; $α_vβ_3$ $pIC_{50}$=6.3; $α_vβ_5$ $pIC_{50}$=6.9; $α_vβ_8$ $pIC_{50}$=7.3.

Figures quoted are Mean $pIC_{50}$ values.

Permeability in MDCK Cells

The passive membrane permeability of Example 1 and Example 4 (both as zwitterion) was determined, in Madin-Darby Canine Kidney-multidrug resistance 1 (MDCKII-MDR1) cells, at pH 7.4 in the presence of the potent P-glycoprotein inhibitor GF120918. Each compound was incubated in duplicate at a concentration of 3-M on each test occasion. In this assay the passive apparent permeability ($P_{app}$) of Example 1 was 71 nm/s (±23 nm/s; n=3 test occasions) and for Example 4 was 17 nm/s (n=2 test occasions).

It was observed that although the two diastereoisomeric Examples 1 and Example 4, had similar affinity in vitro in the $α_vβ_6$ cell adhesion assay (Example 1 $pIC_{50}$=7.9; Example 4 $pIC_{50}$=7.7) they had different permeability in MDCK cells (Example 1 P=71 nm/s and Example 4 P=17 nm/s). This is expected to be reflected by Example 1 having a higher oral availability than Example 4 in vivo in pharmacokinetic studies.

Identification of the Absolute Configuration of Compounds of Structural Formula (I)

Identification of the Absolute Configuration of the 3-fluoropyrrolidin Asymmetric Centre.

The synthesis of the target molecules (IA) commenced separately with each enantiomer of intermediate of structural formula (IX). The enantiomers of (IX) were purchased from Wuxi App Tec. The (+)-benzyl 3-fluoro-3-(hydroxymethyl) pyrrolidine-1-carboxylate provided the diastereoisomer of (IA) with the highest affinity (Example 1 Isomer A). The absolute configuration of (+)-benzyl 3-fluoro-3-(hydroxymethyl) pyrrolidine-1-carboxylate (IX) however was not known, and the following experiments outlined in scheme III were undertaken to establish its configuration.

A racemic mixture of 1-(tert-butoxycarbonyl)-3-fluoropyrrolidin-3-carboxylic acid (XVII) [Chemical Abstract Registry Number 1001754-59-1] (available from Wuxi App Tec) was converted to the N-α-methylbenzyl amide by reaction of the acid (XVII) with first carbonyl diimidazole (CDI), followed by (+)-(R)-α-methylbenzylamine. This provided a diastereoisomeric mixture of amides (Scheme 3, compounds XVIII and XIX), separable by chromatography on silica gel (P. K. Mykhailiuk et. al. Convenient synthesis of enantiopure (R)- and (S)-3-fluoro-3-aminomethylpyrrolidines, *Tetrahedron* 2014, 70, 3011-3017). The configuration of the more polar isomer was established independently by both Mykhailiuk and us by X-ray diffraction studies and shown to be (S)-tert-butyl 3-fluoro-3-(((R)-1-phenylethyl)carbamoyl) pyrrolidine-1-carboxylate [compound (XVIII)] (FIG. 1), and hence for the less polar isomer as (R)-tert-butyl 3-fluoro-3-(((R)-1-phenylethyl)carbamoyl)pyrrolidine-1-carboxylate [compound (XIX)]. Furthermore this provided reference materials for comparison with the compound obtained by the sequence shown in Scheme III. Although our X-ray data on the polar isomer [compound (XVIII)] was in agreement with the X-ray crystal structure reported by Mykhailiuk et. al. the ¹H NMR spectrum differed from the spectrum we obtained. The spectra for the two diastereoisomers [compounds (XVIII) and (XIX)] were very similar; however, there was a small diagnostic difference for the pyrrolidine C4 proton. We observe it at 2.22 ppm. This was reported by Mykhailiuk to be at 2.15 ppm. The (−)-enantiomer of compound of structural formula (IX) [(−)-benzyl 3-fluoro-3-(hydroxymethyl)pyrrolidine-1-carboxylate], which provided the diastereoisomer of (IA) Example 2 (Isomer 1) was hydrogenated over 10% Pd/C in ethanol to remove the CBZ protecting group, and the resulting amine (XX) protected with di-tert-butyl dicarbonate to give (−)-tert-butyl 3-fluoro-3-(hydroxymethyl)pyrrolidine-1-carboxylate (XXI). The latter was oxidised with ruthenium trichloride and sodium periodate in acetonitrile-water. The resulting carboxylic acid (XXII) was then converted to the amide as before using CDI and (+)-(R)-α-methylbenzylamine. This amide was compared with the reference amide samples (XVIII) and (XIX) and it was found to be identical by NMR spectroscopy, optical rotation and chiral HPLC to (R)-tert-butyl 3-fluoro-3-(((R)-1-phenylethyl) carbamoyl) pyrrolidine-1-carboxylate (XIX). Since the (−)-enantiomer of (IX) used in this sequence is the isomer providing diastereoisomers (IA3) and (IA4) (Example 2) then the (+)-enantiomer of (IX), which provided (IA1) and (IA2) (Example 1) has the absolute configuration (S) at the pyrrolidine asymmetric centre.

Scheme III. Identification of the absolute confiuration of the 3-fluoropyrrolidine asymmetric centre.

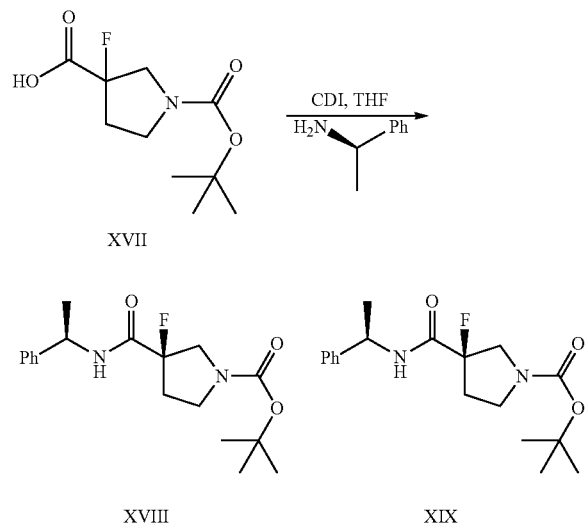

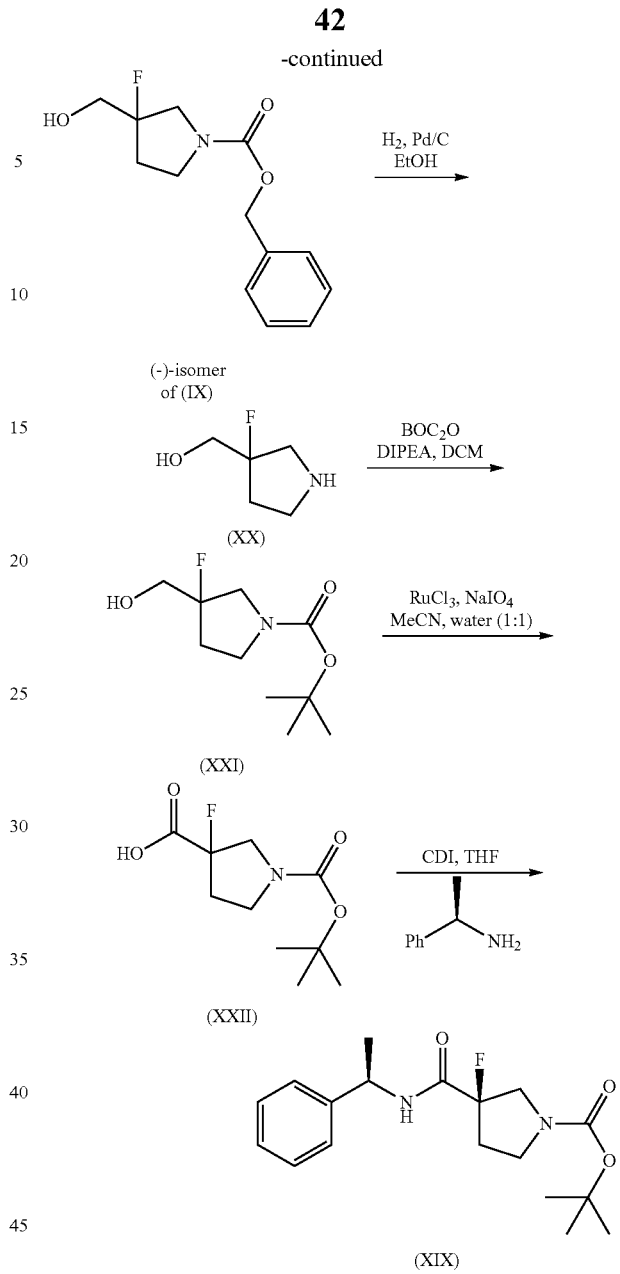

Identification of the Absolute Configuration of the Benzylic Asymmetric Centre

The absolute configuration of the benzylic asymmetric centre of Example 1 Isomer A was obtained by the degradation experiment shown in Scheme IV. Thus, Example 1 Isomer A was treated with methyl iodide in DCM at room temperature overnight to quaternarise the pyrrolidine nitrogen and then potassium carbonate was added, heated to 120° C. for 1 h in a microwave reactor to give (S)-(+)-4-(3-(2-methoxyethoxy)phenyl)dihydrofuran-2(3H)-one (Compound XXIV). The degradation product was compared with authentic (R)-(−)-4-(3-(2-methoxyethoxy)phenyl)dihydrofuran-2(3H)-one (Compound XXV) prepared by addition of (3-(2-methoxyethoxy)phenyl)boronic acid to furan-2(5H)-one using bis(norbornadiene)rhodium (I) tetrafluoroborate as the catalyst and (R)-BINAP as the chiral ligand using the classical Hayashi asymmetric reaction (Hayashi, T. *Tetrahedron Asymmetry*, 1999, 10, 4047-4056) and shown to be the enantiomer of the degradation product, establishing thus the configuration of Example 1 isomer A at its benzylic centre as (S).

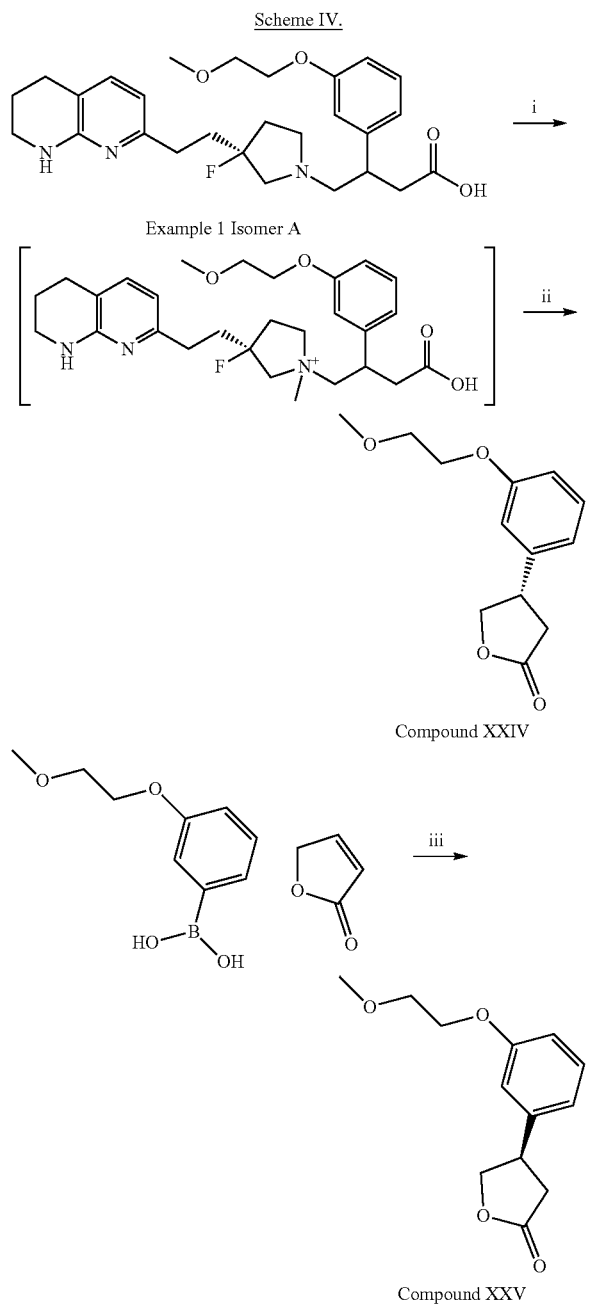

Reagents and conditions: i) MeI, DCM, room temperature, 18 h;
ii) K$_2$CO$_3$, 120° C., 1 h; iii) bis(norbornadiene)rhodium (I)
tetrafluoroborate and (R)-BINAP, KOH, 1,4-dioxane, 100° C., 1 h.

Based on the above experiments to identify the absolute configuration of each asymmetric centre in compound of structural formula (I) the absolute configuration of each Example is summarised as follows:

Example 1 is the compound of structural formula (IA2) (S)-4-((S)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid.

Example 2 is the compound of structural formula (IA1) (R)-4-((S)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid.

Example 3 is the compound of structural formula (IA3) (R)-4-((R)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid.

Example 4 is the compound of structural formula (IA4) (S)-4-((R)-3-fluoro-3-(2-(5,6,7,8-tetrahydro-1,8-naphthyridin-2-yl) ethyl) pyrrolidin-1-yl)-3-(3-(2-methoxyethoxy) phenyl) butanoic acid.

Experimental (S)-tert-butyl 3-fluoro-3-(((R)-1-phenylethyl)carbamoyl)pyrrolidine-1-carboxylate (Compound XVIII) and (R)-tert-Butyl 3-fluoro-3-(((R)-1-phenylethyl)carbamoyl)pyrrolidine-1-carboxylate (Compound XIX)

A solution of (±)-1-(tert-butoxycarbonyl)-3-fluoropyrrolidine-3-carboxylic acid (compound XVII) [1001754-59-1] (available from Wuxi App Tec) (3.00 g, 12.9 mmol) in THF (70 mL) was treated at room temperature with solid CDI (2.5 g, 15.4 mmol) and then the mixture was heated to 80° C. for 1.5 h. (R)-(+)-α-methylbenzylamine (available from Fluka) (1.6 g, 13.2 mmol) was added at this temperature and then the mixture was heated for a further 1.5 h at 80° C. The mixture was diluted with ethyl acetate and washed with dilute HCl, NaHCO$_3$, brine, dried (MgSO$_4$), filtered and allowed to evaporate slowly at room temperature. The mixture was finally concentrated under reduced pressure as no solid crystallised out. The residue was purified by chromatography on silica (2×100 g) cartridges eluting with 0-25% EtOAc-cyclohexane over 40 min. The compound eluting first was obtained as a white foam (1.54 g, 36%): LCMS (System A) RT=1.17 min, ES+ve m/z 337 (M+H)$^+$; $^1$H NMR (500 MHz, CDCl$_3$) 1.43-1.49 (m, 9H), 1.54 (d, J=7.0 Hz, 3H), 2.08-2.19 (m, 1H), 2.37-2.62 (m, 1H), 3.43-3.56 (m, 1H), 3.61-3.93 (m, 3H), 5.14 (quin, J=7.1 Hz, 1H), 6.71-6.76 (m, 1H), 7.27-7.39 (m, 5H) contains about 10% of the more polar diastereoisomer; [α]$_D^{20}$+61 (c=1.27 in MeOH); Analytical Chiral HPLC RT=7.58 min, 90%, and RT=9.53 min, 10% on a Chiralpak AD column (250 mm×4.6 mm), eluting with 10% EtOH-heptane, flow rate=1 mL/min, detecting at 215 nm. A 50 mg portion of this sample was further purified on a silica cartridge (20 g) eluting with 0-25% EtOAc-cyclohexane over 20 min. The appropriate fraction was evaporated under reduced pressure to give an analytically pure sample (30 mg) of (R)-tert-Butyl 3-fluoro-3-(((R)-1-phenylethyl)carbamoyl)pyrrolidine-1-carboxylate (compound XIX) LCMS (SystemC) RT=1.16 min, ES+ve m/z 337 (M+H)$^+$ and 354 (M+NH$_4$)$^+$ and ES−ve m/z 335 (M−H)$^-$; [α]$_D^{20}$+63 (c=0.933 in MeOH).

The second compound eluting from the column (more polar diastereoisomer) (1.2 g, 28%) was crystallised from ether to give white crystals of (S)-tert-butyl 3-fluoro-3-(((R)-1-phenylethyl)carbamoyl)pyrrolidine-1-carboxylate (compound XVIII): mp=113-115° C.; LCMS (SystemC) RT=1.16 min, ES+ve m/z 337 (M+H)$^+$; $^1$H NMR (500 MHz, CDCl$_3$) 1.43-1.48 (m, 9H), 1.54 (d, J=7.0 Hz, 3H), 2.14-2.26 (m, 1H), 2.44-2.70 (m, 1H), 3.46-3.55 (m, 1H), 3.56-3.87 (m, 3H), 5.14 (quin, J=7.1 Hz, 1H), 6.73 (br s, 1H), 7.27-7.40 (m, 5H); [α]$_D^{20}$+73 (c=0.876 in MeOH); Analytical Chiral HPLC RT=9.50 min, 100% on a Chiralpak AD column (250 mm×4.6 mm) eluting with 10% EtOH-heptane, flow rate=1 mL/min, detecting at 215 nm. The absolute configuration of this diastereoisomer was established from an X-ray diffraction study.

(−)-(R)-(3-Fluoropyrrolidin-3-yl) methanol (Compound XX)

A solution of (−)-N-CBZ-3-fluoro-3-(hydroxymethyl) pyrrolidine, (−)-isomer of compound (IX), (available from Wuxi App Tec) (4.0 g, 15.8 mmol) was hydrogenated over 10% Pd/C (400 mg) in ethanol (150 mL) overnight. The catalyst was removed by filtration through celite and washed with ethanol. The filtrate and washings were evaporated under reduced pressure to give the title compound (2.0 g, 106%, contains some ethanol by NMR) as a yellow oil, which solidified into a waxy solid: LCMS (SystemC) RT=0.22 min, ES+ve m/z 120 (M+H)$^+$ and ES−ve m/z 118 (M−H)$^-$. The product was further dried in a blow-down unit under nitrogen at 40° C. $^1$H NMR (500 MHz, CDCl$_3$) 3.82 (dd, J=18.7, 12.5 Hz, 1H), 3.73 (dd, J=22.0, 12.2 Hz, 1H), 3.22-3.15 (m, 1H), 3.23-3.14 (m, 1H), 2.99-2.92 (m, 1H), 2.91 (dd, J=29.1, 13.2 Hz, 1H), 2.66 (br s, 2H), 2.10-1.98 (m, 1H), 1.94-1.81 (m, 1H); $[\alpha]_D^{20}$=−4 (c=1.19 in EtOH).

(−)-(R)-tert-Butyl 3-fluoro-3-(hydroxymethyl)pyrrolidine-1-carboxylate (Compound XXI)

A solution of (R)-(3-fluoropyrrolidin-3-yl)methanol (compound XX) (1.88 g, 15.8 mmol) in DCM (15 mL) and diisopropylethylamine (4.13 mL, 23.7 mmol) was treated with di-tert-butyl dicarbonate (3.79 g, 17 mmol) and the mixture was stirred at 20° C. for 3 h. The mixture was partitioned between 2M HCl and DCM and separated in a phase separator cartridge. The organic layer was concentrated under reduced pressure and the residue was purified by chromatography on a silica cartridge (70 g) eluting with a gradient of 0-50% EtOAc-cyclohexane over 40 min. The fractions were checked by TLC on silica (50% EtOAc-cyclohexane) and stained with KMnO$_4$ solution. Appropriate fractions were combined and evaporated under reduced pressure to give the title compound (2.73 g, 79%) as a colourless oil: LCMS (SystemC) RT=0.79 min, ES+ve m/z 220 (M+H)$^+$ and 439 (2M+H)$^+$; $^1$H NMR (400 MHz, DMSO-d$_6$) δ 1.42 (s, 9H), 1.96-2.14 (m, 2H), 3.32-3.41 (m, 2H), 3.42-3.50 (m, 2H), 3.54-3.61 (m, 1H), 3.62-3.69 (m, 1H), 4.90 (t, J=5.8 Hz, 1H); $[\alpha]_D^{20}$=−28 (c=3.51 in CHCl$_3$).

(R)-tert-Butyl 3-fluoro-3-(((R)-1-phenylethyl)carbamoyl)pyrrolidine-1-carboxylate (Compound XIX)

A solution of (−)-tert-butyl 3-fluoro-3-(hydroxymethyl)pyrrolidine-1-carboxylate (compound XXI) (200 mg, 0.9 mmol) in MeCN (1 mL) and water (1 mL) was treated with RuCl$_3$ (9.5 mg, 0.05 mmol) and sodium periodate (976 mg, 4.5 mmol) and the mixture was stirred at 20° C. for 16 h. The mixture was acidified with 1M HCl (5 mL) and partitioned in DCM. The aqueous phase was re-extracted twice with DCM and the phases separated in a phase-separation cartridge. The organic solution was evaporated in a blow-down unit to give (R)-1-(tert-butoxycarbonyl)-3-fluoropyrrolidine-3-carboxylic acid (compound XXII) (125 mg, 59%): MS ES−ve m/z 232 (M−H)$^-$. The acid (125 mg, 0.54 mmol) was dissolved in ethyl acetate (10 mL) and treated with CDI (360 mg, 2.2 mmol) and the mixture was stirred at room temperature for 1 h and then heated at 50° C. for 0.5 h. The mixture was concentrated in a blow-down unit, the residue was dissolved in THF (6 mL) and treated with (R)-(+)-α-methylbenzylamine (200 mg, 1.9 mmol) and stirred at 20° C. for 1.5 h. The mixture was diluted with ethyl acetate and washed with 2M HCl solution twice, followed by brine. The organic solution was dried (MgSO$_4$) and evaporated under reduced pressure to give a grey solid (290 mg). The residue was dissolved in MeOH-DMSO (1:1; 3 mL) and purified by MDAP on a XSELECT CSH C18 column (150 mm×30 mm i.d. 5 μm packing diameter) at ambient temperature, eluting with a gradient of 30-85% (10 mM ammonium bicarbonate in water adjusted to pH 10 with aq. ammonia solution-acetonitrile) running for 30 min, detecting at 254 nm and collecting the peak with RT=17.4 min, ES+ve m/z 337 (M+H)$^+$. The fraction was concentrated in a blow-down unit at 45° C. under nitrogen and the residual suspension was extracted with EtOAc. The organic solution was washed with 2M HCl twice and then with brine, dried (MgSO$_4$) and evaporated under reduced pressure to give a yellow gum (35 mg). The gum was re-purified by MDAP on a XBridge C18 column (100 mm×19 mm i.d. 5 μm packing diameter) at ambient temperature eluting with a gradient of (10 mM ammonium bicarbonate in water adjusted to pH 10 with aq. ammonia solution-acetonitrile) running for 25 min, detecting at 254 nm) collecting the first fraction (RT=10 min). The solvent was removed in a blow-down unit under nitrogen at 45° C. to give the title compound (16 mg, 5%) as a colourless gum: LCMS (System C) RT=1.16 min, ES+ve m/z 337 (M+H)$^+$, 354 (M+NH$_4$)$^-$; Analytical Chiral HPLC RT=7.58 min, 97.7% on a Chiralpak AD column (250 mm×4.6 mm) eluting with 10% EtOH-heptane, flow rate=1 mL/min, detecting at 215 nm; $[\alpha]_D^{20}$+63 (c=1.15 in MeOH). The $^1$H NMR spectrum (500 MHz, CDCl$_3$) as well as the optical rotation and the chiral HPLC RT all match those of (R)-tert-butyl 3-fluoro-3-(((R)-1-phenylethyl)carbamoyl)pyrrolidine-1-carboxylate (compound XIX).

Determination of the Absolute Configuration of the Benzylic Asymmetric Centre of Example 1 by Degradation to (S)-(+)-4-(3-(2-methoxyethoxy)phenyl) dihydrofuran-2(3H)-one (Compound XXIV)

A solution of 4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid (Example 1 (200 mg, 0.412 mmol) in DCM (20 mL) was treated with iodomethane (0.400 mL, 6.40 mmol) at room temperature and stirred for 18 h. The reaction mixture was concentrated in vacuo to remove the excess iodomethane, the residual solid was re-dissolved in DCM (10 mL) and then potassium carbonate (250 mg, 1.809 mmol) was added. The reaction mixture was heated in a microwave reactor to 120° C. for 1 h. The solution was filtered and concentrated in vacuo and the residual oil was purified by chromatography on a silica column (10 g) eluting with a gradient of 0-100% TBME in cyclohexane, detecting at 220 nm. The relevant fractions were concentrated in vacuo affording (S)-(+)-4-(3-(2-methoxyethoxy)phenyl)dihydrofuran-2(3H)-one (compound XXIV) (80 mg, 82%) as a colourless oil: LCMS (System B) RT=0.80 min, 100%, ES+ve m/z 237 (M+H)$^-$; $^1$H NMR (400 MHz, CDCl$_3$) 7.34-7.26 (m, 1H), 6.92-6.72 (m, 3H), 4.67 (dd, J=9.0, 7.9 Hz, 1H), 4.28 (dd, J=9.1, 8.1 Hz, 1H), 4.20-4.10 (m, 2H), 3.84-3.72 (m, 3H), 3.48 (s, 3H), 2.93 (dd, J=17.5, 8.7 Hz, 1H), 2.68 (dd, J=17.5, 9.0 Hz, 1H); $[\alpha]_D^{22}$=+42 (c=1.06 in CHCl$_3$); Chiral HPLC RT=9.72 min, 100% on a ChiralpakAD column (250 mm×4.6 mm) eluting with 40% EtOH in heptane, flow-rate=1 mL/min, detecting at 215 nm.

Synthesis of Authentic (R)-(−)-4-(3-(2-Methoxyethoxy)phenyl)dihydrofuran-2(3H)-one (Compound XXV) for Comparison with Compound (XXIV)

To a solution of bis(norbornadiene)rhodium (I) tetrafluoroborate (available from Aldrich) (37.4 mg, 0.100 mmol), (R)-BINAP (125 mg, 0.200 mmol) and (3-(2-methoxyethoxy)phenyl)boronic acid (available from Enamine) (980 mg, 5.00 mmol) in 1,4-dioxane (10 mL) was added furan-2(5H)-one (available from Alfa Aesar) (0.142 mL, 2.0 mmol) and aqueous KOH (3.8 M, 1.053 mL, 4.00 mmol). The resulting solution was heated to 100° C. for 1 h in a microwave reactor. The reaction mixture was allowed to cool and partitioned between water (20 mL) and DCM (20 mL). The layers were separated and the organic layer was passed through a hydrophobic frit and concentrated in vacuo. The residual oil was purified by chromatography on a KPNH column (50 g) eluting with a gradient of 0-100% TBME in cyclohexane over 45 min, detecting at 220 nm. The relevant fractions were concentrated in vacuo to give the title compound (101 mg, 21%) as a colourless oil: LCMS (System B) RT=0.80 min, 100%, ES+ve m/z 237 (M+H)⁻; $[\alpha]_D^{23}$=−37 (c=1.10 in CHCl$_3$); Chiral HPLC RT=11.82 min, 94% and RT=9.67 min, 6% on a Chiralpak AD column (250 mm×4.6 mm) eluting with 40% EtOH in heptane, flow rate=1 mL/min, detecting at 215 nm, indicating that the title compound is the enantiomer of compound (XXIV).

Hence: Example 1 is (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

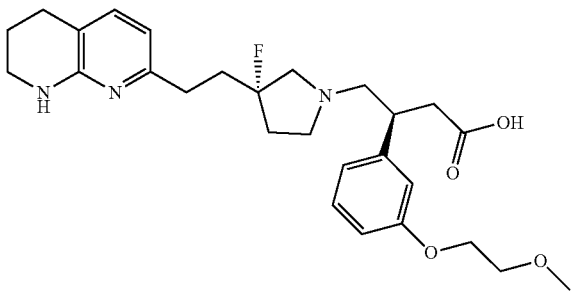 [SMILES: COCCOc1cccc([C@H](CC(=O)O)CN2CC[C@@](F)(CCc3ccc4c(n3)NCCC4)C2)c1]

And Example 2 is (R)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid.

The invention claimed is:

1. A method of treating a fibrotic disease or disorder in a human in need thereof comprising administering to the human a therapeutically effective amount of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

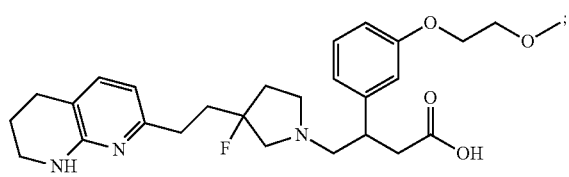 [SMILES: COCCOc1cccc(C(CC(=O)O)CN2CCC(F)(CCc3ccc4c(n3)NCCC4)C2)c1]

or a pharmaceutically acceptable salt thereof.

2. A method of treating a fibrotic disease or disorder in a human in need thereof comprising administering to the human a therapeutically effective amount of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

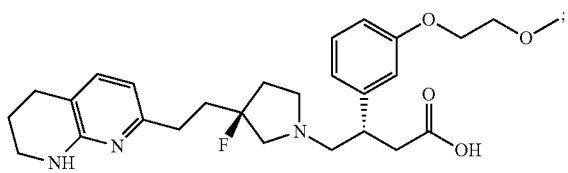 [SMILES: COCCOc1cccc([C@H](CC(=O)O)CN2CC[C@@](F)(CCc3ccc4c(n3)NCCC4)C2)c1]

or a pharmaceutically acceptable salt thereof.

3. A combination comprising of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

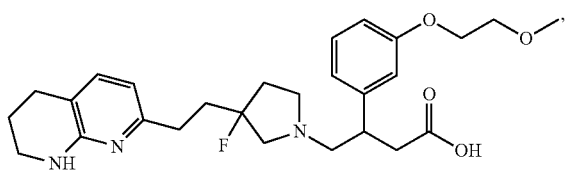 [SMILES: COCCOc1cccc(C(CC(=O)O)CN2CCC(F)(CCc3ccc4c(n3)NCCC4)C2)c1]

or a pharmaceutically acceptable salt thereof, and a therapeutically active agent.

4. A combination comprising of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

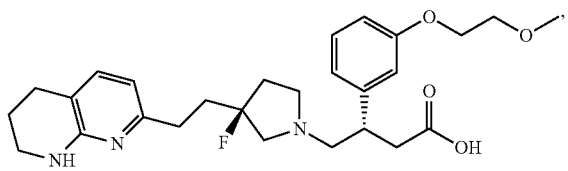 [SMILES: COCCOc1cccc([C@H](CC(=O)O)CN2CC[C@@](F)(CCc3ccc4c(n3)NCCC4)C2)c1]

or a pharmaceutically acceptable salt thereof, and a therapeutically active agent.

5. The combination according to claim 3, wherein the therapeutically active agent is an inhibitor of TGFβ synthesis.

6. The combination according to claim 4, wherein the therapeutically active agent is an inhibitor of TGFβ synthesis.

7. The combination according to claim 3, wherein the therapeutically active agent is pirfenidone.

8. The combination according to claim 4, wherein the therapeutically active agent is pirfenidone.

9. The combination according to claim 3, wherein the therapeutically active agent is nintedanib.

10. The combination according to claim 4, wherein the therapeutically active agent is nintedanib.

11. The combination according to claim 3, wherein the therapeutically active agent is an anti αvβ6 receptor antibody or antigen binding fragment thereof.

12. The combination according to claim 4, wherein the therapeutically active agent is an anti αvβ6 receptor antibody or antigen binding fragment thereof.

13. A method of treating a fibrotic disease or disorder in a human in need thereof comprising administering a therapeutically effective amount to the human of a combination comprising 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

or a pharmaceutically acceptable salt thereof, and a therapeutically active agent.

14. A method of treating a fibrotic disease or disorder in a human in need thereof comprising administering a therapeutically effective amount to the human of a combination comprising (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

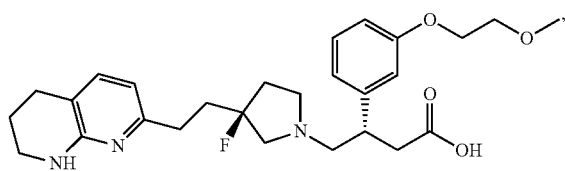 [SMILES: COCCOc1cccc([C@H](CC(=O)O)CN2CC[C@@](F)(CCc3ccc4c(n3)NCCC4)C2)c1]

or a pharmaceutically acceptable salt thereof, and a therapeutically active agent.

15. The method according to claim 13, wherein the therapeutically active agent is an inhibitor of TGFβ synthesis.

16. The method according to claim 14, wherein the therapeutically active agent is an inhibitor of TGFβ synthesis.

17. The method according to claim 13, wherein the therapeutically active agent is an anti αvβ6 receptor antibody or antigen binding fragment thereof.

18. The method according to claim 14, wherein the therapeutically active agent is an anti αvβ6 receptor antibody or antigen binding fragment thereof.

19. A method of treating idiopathic pulmonary fibrosis in a human comprising administering to the human in need thereof a therapeutically effective amount of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

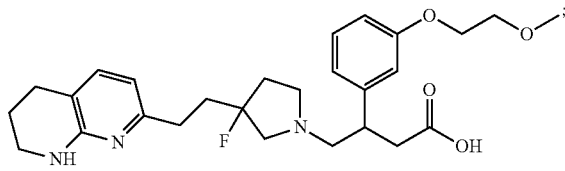 [SMILES: COCCOc1cccc(C(CC(=O)O)CN2CCC(F)(CCc3ccc4c(n3)NCCC4)C2)c1]

or a pharmaceutically acceptable salt thereof.

20. A method of treating idiopathic pulmonary fibrosis in a human comprising administering to the human in in need thereof a therapeutically effective amount of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

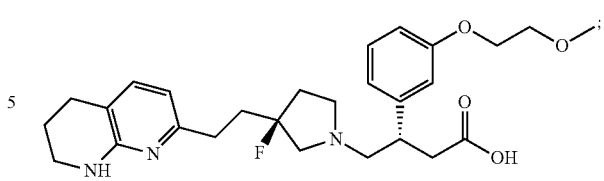

or a pharmaceutically acceptable salt thereof.

21. A method of treating pulmonary fibrosis in a human comprising administering to the human in need thereof a therapeutically effective amount of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

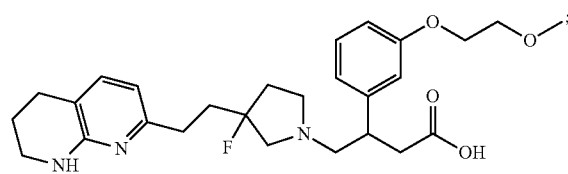 [SMILES: COCCOc1cccc(C(CC(=O)O)CN2CCC(F)(CCc3ccc4c(n3)NCCC4)C2)c1]

or a pharmaceutically acceptable salt thereof.

22. The method of treating according to claim 21, wherein the pulmonary fibrosis is non-specific interstitial pneumonia or usual interstitial pneumonia.

23. A method of treating pulmonary fibrosis in a human comprising administering to the human in need thereof a therapeutically effective amount of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

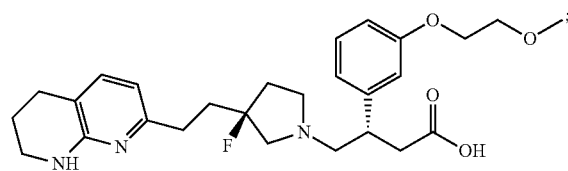

or a pharmaceutically acceptable salt thereof.

24. The method according to claim 23, wherein the pulmonary fibrosis is non-specific interstitial pneumonia or usual interstitial pneumonia.

25. A method of treating hepatic fibrosis in a human comprising administering to the human in need thereof a therapeutically effective amount of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

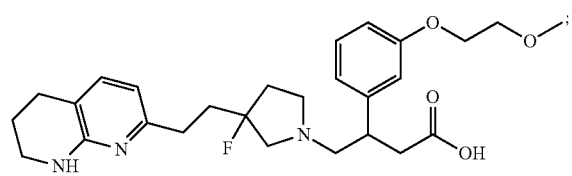 [SMILES: COCCOc1cccc(C(CC(=O)O)CN2CCC(F)(CCc3ccc4c(n3)NCCC4)C2)c1]

or a pharmaceutically acceptable salt thereof.

26. The method according to claim 25, wherein the hepatic fibrosis is viral induced fibrosis, hepatitis C, primary biliary cirrhosis, alcoholic liver disease, non-alcoholic fatty liver disease, or non-alcoholic steatohepatitis.

27. A method of treating hepatic fibrosis in a human comprising administering to the human in in need thereof a therapeutically effective amount of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

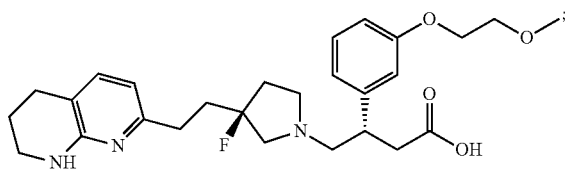

or a pharmaceutically acceptable salt thereof.

28. The method according to claim 27, wherein the hepatic fibrosis is viral induced fibrosis, hepatitis C, primary biliary cirrhosis, alcoholic liver disease, non-alcoholic fatty liver disease, or non-alcoholic steatohepatitis.

29. A method of treating renal fibrosis in a human comprising administering to the human in need thereof a therapeutically effective amount of 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

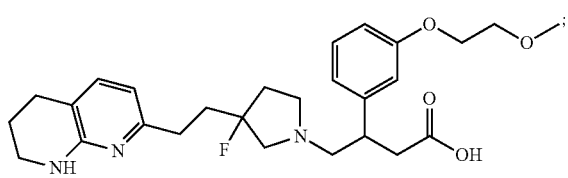 [SMILES: COCCOc1cccc(C(CC(=O)O)CN2CCC(F)(CCc3ccc4c(n3)NCCC4)C2)c1]

or a pharmaceutically acceptable salt thereof.

30. The method according to claim 29, wherein the renal fibrosis is diabetic nephropathy, IgA nephropathy, or focal segmental glomerulosclerosis.

31. A method of treating renal fibrosis in a human comprising administering to the human in in need thereof a therapeutically effective amount of (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

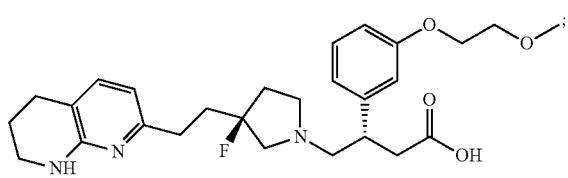 [SMILES: COCCOc1cccc([C@H](CC(=O)O)CN2CC[C@@](F)(CCc3ccc4c(n3)NCCC4)C2)c1]

or a pharmaceutically acceptable salt thereof.

32. The method according to claim 31, wherein the renal fibrosis is diabetic nephropathy, IgA nephropathy, or focal segmental glomerulosclerosis.

33. A method of treating idiopathic pulmonary fibrosis in a human in need thereof comprising administering a therapeutically effective amount to the human of a combination comprising 4-(3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

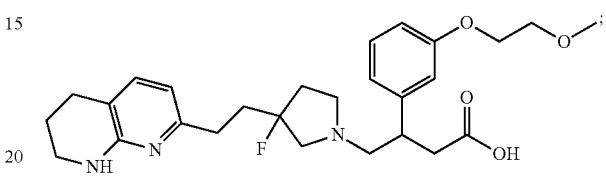

or a pharmaceutically acceptable salt thereof, and a therapeutically active agent.

34. A method of treating idiopathic pulmonary fibrosis in a human in need thereof comprising administering a therapeutically effective amount to the human of a combination comprising (S)-4-((S)-3-fluoro-3-(2-(5,6,7,8-tetrahydro-1,8-naphthyridin-2-yl)ethyl)pyrrolidin-1-yl)-3-(3-(2-methoxyethoxy)phenyl)butanoic acid

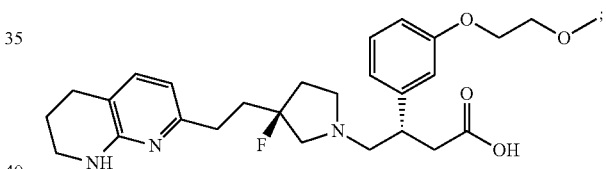

or a pharmaceutically acceptable salt thereof, and a therapeutically active agent.

35. The method according to claim 33, wherein the therapeutically active agent is pirfenidone.

36. The method according to claim 34, wherein the therapeutically active agent is pirfenidone.

37. The method according to claim 33, wherein the therapeutically active agent is nintedanib.

38. The method according to claim 34, wherein the therapeutically active agent is nintedanib.

* * * * *